United States Patent
Morrison et al.

(10) Patent No.: US 10,918,816 B2
(45) Date of Patent: *Feb. 16, 2021

(54) COMPLIANCE MONITORING MODULE FOR A BREATH-ACTUATED INHALER

(71) Applicant: Norton (Waterford) Limited, Waterford (IE)

(72) Inventors: Mark Steven Morrison, Basking Ridge, NJ (US); Douglas E. Weitzel, Hamilton, NJ (US); Enrique Calderon Oliveras, Waterford (IE); Daniel Buck, Waterford (IE)

(73) Assignee: Norton (Waterford) Limited, Waterford (IE)

( * ) Notice: Subject to any disclaimer, the term of this patent is extended or adjusted under 35 U.S.C. 154(b) by 108 days.

This patent is subject to a terminal disclaimer.

(21) Appl. No.: 16/148,075

(22) Filed: Oct. 1, 2018

(65) Prior Publication Data

US 2019/0030267 A1 Jan. 31, 2019

Related U.S. Application Data

(63) Continuation of application No. 15/681,126, filed on Aug. 18, 2017, now Pat. No. 10,569,034, which is a
(Continued)

(51) Int. Cl.
*A61M 16/00* (2006.01)
*A61M 15/00* (2006.01)

(52) U.S. Cl.
CPC ...... *A61M 15/0065* (2013.01); *A61M 15/008* (2014.02); *A61M 15/009* (2013.01);
(Continued)

(58) Field of Classification Search
CPC .............. A61M 15/00; A61M 15/0001; A61M 15/0021; A61M 15/0025; A61M 15/0026;
(Continued)

(56) References Cited

U.S. PATENT DOCUMENTS

| 4,157,530 A | 6/1979 | Merz et al. |
| 4,984,158 A | 1/1991 | Hillsman |

(Continued)

FOREIGN PATENT DOCUMENTS

| CN | 1700934 A | 11/2005 |
| CN | 105163784 A | 12/2015 |

(Continued)

*Primary Examiner* — Joseph D. Boecker
(74) *Attorney, Agent, or Firm* — Flaster Greenberg P.C.

(57) ABSTRACT

A compliance monitoring module for a breath-actuated inhaler comprising: a miniature pressure sensor, a sensor port of said sensor being pneumatically coupled to a flow channel through which a user can inhale; a processor configured to: receive a signal originating from a dosing mechanism of the inhaler indicating that medication has been released; receive data from a sensing element of the sensor; and based on said signal from said dosing mechanism and said data from said sensing element, make a determination that inhalation of a breath containing medication through said flow channel complies with one or more predetermined requirements for successful dosing; and a transmitter configured to, responsive to said determination, issue a dosing report.

20 Claims, 15 Drawing Sheets

Related U.S. Application Data continuation of application No. 15/155,808, filed on May 16, 2016, now Pat. No. 9,782,550, which is a continuation of application No. 15/155,400, filed on May 16, 2016, now Pat. No. 9,782,551, which is a continuation of application No. PCT/US2015/047366, filed on Aug. 28, 2015.

(60) Provisional application No. 62/043,120, filed on Aug. 28, 2014.

(52) U.S. Cl.
CPC .... *A61M 15/0026* (2014.02); *A61M 15/0071* (2014.02); *A61M 15/0091* (2013.01); *A61M 15/00* (2013.01); *A61M 2205/3331* (2013.01); *A61M 2205/3576* (2013.01); *A61M 2205/3584* (2013.01); *A61M 2205/50* (2013.01); *A61M 2205/58* (2013.01); *A61M 2205/583* (2013.01); *A61M 2205/584* (2013.01); *A61M 2205/587* (2013.01); *A61M 2209/088* (2013.01)

(58) Field of Classification Search
CPC .......... A61M 15/0065; A61M 15/0071; A61M 15/008; A61M 15/009; A61M 15/0091; A61M 15/0098; A61M 2205/3331; A61M 2205/3358; A61M 11/00; A61M 2016/0027; A24F 47/008; A24F 40/00; A24F 40/51
See application file for complete search history.

(56) References Cited

U.S. PATENT DOCUMENTS

| | | | |
|---|---|---|---|
| 5,333,106 A * | 7/1994 | Lanpher | G09B 5/02 128/200.12 |
| 5,363,842 A * | 11/1994 | Mishelevich | A61B 8/0875 128/200.14 |
| 5,740,793 A | 4/1998 | Hodson et al. | |
| 5,809,997 A | 9/1998 | Wolf | |
| 5,839,429 A | 11/1998 | Marnfeldt et al. | |
| 5,842,468 A | 12/1998 | Denyet et al. | |
| 5,887,586 A | 3/1999 | Dahlback et al. | |
| 6,012,454 A | 1/2000 | Hodson et al. | |
| 6,029,662 A | 2/2000 | Marcon et al. | |
| 6,076,521 A | 6/2000 | Lindahl et al. | |
| 6,119,684 A | 9/2000 | Nohl et al. | |
| 6,182,655 B1 | 2/2001 | Keller et al. | |
| 6,269,829 B1 | 8/2001 | Chen et al. | |
| 6,285,731 B1 | 9/2001 | Marnfeldt et al. | |
| 6,390,088 B1 | 5/2002 | Sprenger et al. | |
| 6,431,399 B2 | 8/2002 | Gabel et al. | |
| 6,615,824 B2 | 9/2003 | Power | |
| 6,651,651 B1 * | 11/2003 | Bonney | A61M 15/009 128/200.23 |
| 6,752,145 B1 | 6/2004 | Bonney et al. | |
| 6,752,147 B1 | 6/2004 | Goldemann et al. | |
| 6,839,604 B2 | 1/2005 | Godfrey et al. | |
| 6,845,770 B2 | 1/2005 | Klimowicz et al. | |
| 6,932,083 B2 | 8/2005 | Jones et al. | |
| 6,958,691 B1 | 10/2005 | Anderson et al. | |
| 6,978,780 B1 | 12/2005 | Marnfeldt et al. | |
| 6,990,975 B1 | 1/2006 | Jones et al. | |
| 7,009,517 B2 | 3/2006 | Wood | |
| 7,072,738 B2 | 7/2006 | Bonney et al. | |
| 7,151,456 B2 | 12/2006 | Godfrey | |
| 7,191,777 B2 | 3/2007 | Brand et al. | |
| 7,198,172 B2 | 4/2007 | Harvey et al. | |
| 7,233,228 B2 | 6/2007 | Lintell et al. | |
| 7,249,687 B2 | 7/2007 | Anderson et al. | |
| 7,322,355 B2 | 1/2008 | Jones et al. | |
| 7,347,200 B2 | 3/2008 | Jones et al. | |
| 7,383,837 B2 | 6/2008 | Robertson et al. | |
| 7,424,888 B2 | 9/2008 | Harvey et al. | |
| 7,495,546 B2 | 2/2009 | Lintell et al. | |
| 7,661,423 B2 | 2/2010 | Brand et al. | |
| 7,819,116 B2 | 10/2010 | Brand et al. | |
| 7,837,648 B2 | 11/2010 | Blair et al. | |
| 8,231,573 B2 | 7/2012 | Edwards et al. | |
| 8,240,301 B2 | 8/2012 | Spaargaren et al. | |
| 8,251,059 B2 | 8/2012 | Nishibayashi et al. | |
| 8,424,517 B2 | 4/2013 | Sutherland et al. | |
| 8,439,033 B2 | 5/2013 | Gumaste et al. | |
| 8,464,707 B2 | 6/2013 | Jongejan et al. | |
| 8,547,239 B2 | 10/2013 | Peatfield et al. | |
| 8,550,069 B2 | 10/2013 | Alelov et al. | |
| 8,567,394 B2 | 10/2013 | Herder et al. | |
| 8,807,131 B1 | 8/2014 | Tunnell et al. | |
| 8,960,189 B2 | 2/2015 | Morrison et al. | |
| 8,997,735 B2 | 4/2015 | Zierenberg et al. | |
| 9,056,174 B2 | 6/2015 | Bradshaw et al. | |
| 9,162,031 B2 | 10/2015 | Gumaste et al. | |
| 9,174,009 B2 | 11/2015 | Peatfield et al. | |
| 9,188,579 B2 | 11/2015 | Shen et al. | |
| 9,242,056 B2 | 1/2016 | Andersen et al. | |
| 9,339,616 B2 | 5/2016 | Denny et al. | |
| 9,364,619 B2 | 6/2016 | Overfield et al. | |
| 9,381,313 B2 | 7/2016 | Bari et al. | |
| 9,427,534 B2 | 8/2016 | Bruin et al. | |
| 9,439,455 B2 | 9/2016 | Alarcon et al. | |
| 9,463,291 B2 | 10/2016 | Imran et al. | |
| 9,468,729 B2 | 10/2016 | Sutherland et al. | |
| 9,542,826 B2 | 1/2017 | Edwards et al. | |
| 9,550,031 B2 | 1/2017 | Van Sickle et al. | |
| 9,694,147 B2 | 7/2017 | Peatfield et al. | |
| 9,736,642 B2 | 8/2017 | Ostrander et al. | |
| 9,839,398 B2 | 12/2017 | Yamamori et al. | |
| 9,911,308 B2 | 3/2018 | Edwards et al. | |
| 9,956,360 B2 | 5/2018 | Germinario et al. | |
| 9,962,507 B2 | 5/2018 | Germinario et al. | |
| 9,962,508 B2 | 5/2018 | Bruin et al. | |
| 10,016,134 B2 | 7/2018 | Hansen et al. | |
| 10,046,121 B2 | 8/2018 | Kolb et al. | |
| 10,569,034 B2 * | 2/2020 | Morrison | A61M 15/0065 |
| 2002/0000225 A1 | 1/2002 | Schuler et al. | |
| 2002/0073996 A1 | 6/2002 | O'Leary | |
| 2002/0134372 A1 | 9/2002 | Loffler et al. | |
| 2002/0134374 A1 | 9/2002 | Loffler et al. | |
| 2002/0153006 A1 | 10/2002 | Zimlich, Jr. et al. | |
| 2002/0185128 A1 | 12/2002 | Theobald | |
| 2003/0079744 A1 | 5/2003 | Bonney et al. | |
| 2003/0101991 A1 * | 6/2003 | Trueba | A61M 15/025 128/200.14 |
| 2003/0127538 A1 | 7/2003 | Patel et al. | |
| 2003/0150446 A1 | 8/2003 | Patel et al. | |
| 2003/0192535 A1 | 10/2003 | Christrup et al. | |
| 2003/0205229 A1 * | 11/2003 | Crockford | A61M 15/0088 128/204.23 |
| 2003/0226837 A1 | 12/2003 | Blake et al. | |
| 2004/0035420 A1 | 2/2004 | Davies et al. | |
| 2004/0081624 A1 | 4/2004 | Nguyen et al. | |
| 2004/0089299 A1 | 5/2004 | Bonney et al. | |
| 2004/0094152 A1 | 5/2004 | Harvey et al. | |
| 2004/0117062 A1 | 6/2004 | Bonney et al. | |
| 2004/0158349 A1 | 8/2004 | Bonney et al. | |
| 2004/0172162 A1 | 9/2004 | Bonney et al. | |
| 2004/0187869 A1 * | 9/2004 | Bjorndal | G09B 23/28 128/203.15 |
| 2005/0043674 A1 | 2/2005 | Blair | |
| 2005/0066961 A1 | 3/2005 | Rand | |
| 2005/0119604 A1 | 6/2005 | Bonney et al. | |
| 2005/0161467 A1 | 7/2005 | Jones | |
| 2005/0172954 A1 | 8/2005 | Smith et al. | |
| 2005/0174216 A1 | 8/2005 | Lintell | |
| 2005/0177275 A1 | 8/2005 | Harvey et al. | |
| 2005/0183718 A1 | 8/2005 | Wuttke et al. | |
| 2005/0217666 A1 | 10/2005 | Fink et al. | |
| 2005/0228341 A1 | 10/2005 | Edgerley | |
| 2005/0247312 A1 | 11/2005 | Davies et al. | |
| 2005/0251289 A1 | 11/2005 | Bonney et al. | |
| 2005/0258182 A1 | 11/2005 | Anderson | |
| 2005/0268908 A1 | 12/2005 | Bonney et al. | |

(56) References Cited

U.S. PATENT DOCUMENTS

| | | |
|---|---|---|
| 2006/0027233 A1 | 2/2006 | Zierenberg et al. |
| 2006/0102175 A1 | 5/2006 | Nelson |
| 2006/0196504 A1 | 9/2006 | Augustyn et al. |
| 2007/0052544 A1 | 3/2007 | Lintell |
| 2007/0056585 A1 | 3/2007 | Davies et al. |
| 2007/0062525 A1 | 3/2007 | Bonney et al. |
| 2007/0064302 A1 | 3/2007 | Johnson et al. |
| 2007/0145065 A1 | 6/2007 | Anderson et al. |
| 2007/0225587 A1 | 9/2007 | Burnell et al. |
| 2008/0017189 A1 | 1/2008 | Ruckdeschel et al. |
| 2008/0017193 A1 | 1/2008 | Jones et al. |
| 2008/0042823 A1 | 2/2008 | Heasley et al. |
| 2008/0178872 A1 | 7/2008 | Genova et al. |
| 2008/0230057 A1 | 9/2008 | Sutherland et al. |
| 2008/0268060 A1 | 10/2008 | Nguyen et al. |
| 2008/0295827 A1 | 12/2008 | Kobayashi et al. |
| 2008/0314383 A1 | 12/2008 | Barney et al. |
| 2009/0114219 A1* | 5/2009 | Ferris ............... A61M 15/0095 128/203.15 |
| 2009/0125324 A1 | 5/2009 | Keravich et al. |
| 2009/0151721 A1 | 6/2009 | Spaargaren et al. |
| 2009/0178678 A1 | 7/2009 | O'Leary et al. |
| 2009/0221308 A1 | 9/2009 | Lerner et al. |
| 2010/0050770 A1 | 3/2010 | Barger et al. |
| 2010/0242960 A1 | 9/2010 | Zangerle et al. |
| 2010/0250280 A1 | 9/2010 | Sutherland et al. |
| 2011/0011393 A1 | 1/2011 | Geser et al. |
| 2011/0036346 A1 | 2/2011 | Cohen et al. |
| 2011/0048415 A1 | 3/2011 | Zierenberg et al. |
| 2011/0108030 A1 | 5/2011 | Blair et al. |
| 2011/0282693 A1 | 11/2011 | Craft et al. |
| 2011/0283997 A1 | 11/2011 | Walsh et al. |
| 2012/0055472 A1 | 3/2012 | Brunnberg et al. |
| 2012/0132199 A1 | 5/2012 | Kiesewetter |
| 2012/0285447 A1* | 11/2012 | Schipper ............... A61B 5/1117 128/200.16 |
| 2013/0008436 A1* | 1/2013 | Von Hollen ...... A61M 15/0005 128/200.14 |
| 2013/0125880 A1 | 5/2013 | Holakovsky et al. |
| 2013/0133643 A1 | 5/2013 | Hodson et al. |
| 2013/0146613 A1 | 6/2013 | Balthes |
| 2013/0206142 A1 | 8/2013 | Dudley et al. |
| 2013/0269685 A1 | 10/2013 | Wachtel |
| 2013/0284192 A1 | 10/2013 | Peleg et al. |
| 2013/0298905 A1* | 11/2013 | Levin ............... A24F 47/008 128/202.21 |
| 2013/0323699 A1 | 12/2013 | Edwards et al. |
| 2014/0000603 A1 | 1/2014 | Hosemann et al. |
| 2014/0746310 | 3/2014 | Newton et al. |
| 2014/0106324 A1 | 4/2014 | Adams et al. |
| 2014/0116426 A1 | 5/2014 | Mullinger et al. |
| 2014/0153794 A1 | 6/2014 | Varaklis |
| 2014/0158704 A1 | 6/2014 | Anderson et al. |
| 2014/0182584 A1 | 7/2014 | Sutherland et al. |
| 2014/0261414 A1 | 9/2014 | Weitzel et al. |
| 2014/0352690 A1 | 12/2014 | Kolb et al. |
| 2015/0100335 A1 | 4/2015 | Englehard et al. |
| 2015/0136158 A1 | 5/2015 | Stevens et al. |
| 2015/0174349 A1* | 6/2015 | Tunnell ............... A61M 11/005 128/200.14 |
| 2015/0231336 A1 | 8/2015 | Edwards et al. |
| 2015/0245660 A1 | 9/2015 | Lord et al. |
| 2015/0273165 A1 | 10/2015 | Hadash et al. |
| 2015/0283341 A1 | 10/2015 | Adams et al. |
| 2016/0007913 A1 | 1/2016 | Darket et al. |
| 2016/0051776 A1 | 2/2016 | Von Hollen |
| 2016/0082208 A1 | 3/2016 | Ballam et al. |
| 2016/0128389 A1 | 5/2016 | Lamb et al. |
| 2016/0144141 A1 | 5/2016 | Biswas et al. |
| 2016/0166766 A1 | 6/2016 | Schuster et al. |
| 2016/0166787 A1 | 6/2016 | Morrison et al. |
| 2016/0228657 A1 | 8/2016 | Sutherland et al. |
| 2016/0256639 A1 | 9/2016 | Van Sickle et al. |
| 2016/0314256 A1 | 10/2016 | Su et al. |
| 2016/0374397 A1* | 12/2016 | Jordan ............... G05B 15/02 131/329 |
| 2017/0079557 A1 | 3/2017 | Lauk et al. |
| 2017/0109493 A1 | 4/2017 | Hogg et al. |
| 2017/0140125 A1 | 5/2017 | Hogg et al. |
| 2017/0150757 A1 | 6/2017 | Worm et al. |
| 2017/0164892 A1 | 6/2017 | Sezan et al. |
| 2017/0173279 A1 | 6/2017 | Sutherland et al. |
| 2017/0246406 A1 | 8/2017 | Sutherland et al. |
| 2017/0258993 A1 | 9/2017 | Pizzochero et al. |
| 2017/0262613 A1 | 9/2017 | Ljungberg et al. |
| 2017/0274162 A1* | 9/2017 | Morrison .......... A61M 15/0065 |
| 2017/0290527 A1* | 10/2017 | Morrison ............ A61M 16/021 |
| 2017/0325734 A1 | 11/2017 | Sutherland et al. |
| 2017/0363673 A1 | 12/2017 | Mukherjee et al. |
| 2018/0011988 A1 | 1/2018 | Ziegler et al. |
| 2018/0052964 A1 | 2/2018 | Adelson et al. |
| 2018/0085540 A1 | 3/2018 | Dantsker et al. |
| 2018/0125365 A1 | 5/2018 | Hunter et al. |
| 2018/0161530 A1 | 6/2018 | Ganton et al. |

FOREIGN PATENT DOCUMENTS

| | | |
|---|---|---|
| DE | 4422710 C1 | 9/1995 |
| DE | 29802035 U1 | 6/1999 |
| DE | 102004009434 A1 | 12/2005 |
| DE | 102004009435 A1 | 12/2005 |
| DE | 102007058112 A1 | 6/2009 |
| EP | 0470154 A1 | 2/1992 |
| EP | 472598 A1 | 3/1992 |
| EP | 667168 A1 | 8/1995 |
| EP | 705614 A1 | 4/1996 |
| EP | 0767683 A1 | 4/1997 |
| EP | 794805 A1 | 9/1997 |
| EP | 802813 A1 | 10/1997 |
| EP | 1028768 A1 | 8/2000 |
| EP | 1030704 A1 | 8/2000 |
| EP | 1037683 A1 | 9/2000 |
| EP | 1056659 A1 | 12/2000 |
| EP | 1067980 A1 | 1/2001 |
| EP | 1067981 A1 | 1/2001 |
| EP | 1068591 A1 | 1/2001 |
| EP | 1083841 A1 | 3/2001 |
| EP | 1107810 A1 | 6/2001 |
| EP | 1159020 A1 | 12/2001 |
| EP | 1181068 A1 | 2/2002 |
| EP | 1220802 A1 | 7/2002 |
| EP | 1223855 A1 | 7/2002 |
| EP | 1224600 A1 | 7/2002 |
| EP | 1224601 A1 | 7/2002 |
| EP | 1235604 A1 | 9/2002 |
| EP | 1235606 A1 | 9/2002 |
| EP | 1235607 A1 | 9/2002 |
| EP | 1235608 A2 | 9/2002 |
| EP | 1235609 A2 | 9/2002 |
| EP | 1255580 A2 | 11/2002 |
| EP | 1257311 A1 | 11/2002 |
| EP | 1267970 A1 | 1/2003 |
| EP | 1272907 A2 | 1/2003 |
| EP | 1278569 A1 | 1/2003 |
| EP | 1292348 A1 | 3/2003 |
| EP | 1292933 A1 | 3/2003 |
| EP | 1301230 A1 | 4/2003 |
| EP | 1313523 A1 | 5/2003 |
| EP | 1326668 A2 | 7/2003 |
| EP | 1326669 A1 | 7/2003 |
| EP | 1330281 A1 | 7/2003 |
| EP | 1330282 A1 | 7/2003 |
| EP | 1330283 A2 | 7/2003 |
| EP | 1370316 A1 | 12/2003 |
| EP | 1370317 A1 | 12/2003 |
| EP | 1372570 A2 | 1/2004 |
| EP | 1374137 A2 | 1/2004 |
| EP | 1377332 A1 | 1/2004 |
| EP | 1388115 A2 | 2/2004 |
| EP | 1436031 A1 | 7/2004 |
| EP | 1445214 A1 | 8/2004 |
| EP | 1448257 A1 | 8/2004 |
| EP | 1461103 A1 | 9/2004 |

(56) References Cited

FOREIGN PATENT DOCUMENTS

| | | | |
|---|---|---|---|
| EP | 1467789 | A1 | 10/2004 |
| EP | 1467790 | A1 | 10/2004 |
| EP | 1471868 | A1 | 11/2004 |
| EP | 1471960 | A1 | 11/2004 |
| EP | 1471961 | A1 | 11/2004 |
| EP | 1474196 | A1 | 11/2004 |
| EP | 1474198 | A1 | 11/2004 |
| EP | 1495778 | A2 | 1/2005 |
| EP | 1499275 | A2 | 1/2005 |
| EP | 1499276 | A2 | 1/2005 |
| EP | 1499373 | A2 | 1/2005 |
| EP | 1499376 | A1 | 1/2005 |
| EP | 1525018 | A1 | 4/2005 |
| EP | 1534367 | A1 | 6/2005 |
| EP | 1534368 | A1 | 6/2005 |
| EP | 1537887 | A1 | 6/2005 |
| EP | 1554194 | A2 | 7/2005 |
| EP | 1330282 | B1 | 12/2005 |
| EP | 1625491 | A1 | 2/2006 |
| EP | 1644268 | A1 | 4/2006 |
| EP | 1651296 | A1 | 5/2006 |
| EP | 1663360 | A1 | 6/2006 |
| EP | 1135056 | B1 | 8/2006 |
| EP | 1696988 | A2 | 9/2006 |
| EP | 1712178 | A2 | 10/2006 |
| EP | 1720659 | A1 | 11/2006 |
| EP | 1720662 | A1 | 11/2006 |
| EP | 1720663 | A1 | 11/2006 |
| EP | 1812778 | A2 | 8/2007 |
| EP | 1836452 | A2 | 9/2007 |
| EP | 1868570 | A2 | 12/2007 |
| EP | 1917108 | A2 | 5/2008 |
| EP | 1992381 | A1 | 11/2008 |
| EP | 2023989 | A1 | 2/2009 |
| EP | 2220624 | A1 | 8/2010 |
| EP | 2266650 | A1 | 12/2010 |
| EP | 2398538 | A2 | 12/2011 |
| EP | 2436453 | A1 | 4/2012 |
| EP | 2577573 | A1 | 4/2013 |
| EP | 2582468 | A1 | 4/2013 |
| EP | 2667776 | A2 | 12/2013 |
| EP | 2686049 | A1 | 1/2014 |
| EP | 2714280 | A2 | 4/2014 |
| EP | 2839857 | A1 | 2/2015 |
| EP | 2865403 | A1 | 4/2015 |
| EP | 2903672 | A1 | 8/2015 |
| EP | 3228345 | A1 | 10/2017 |
| GB | 2294402 | A | 5/1996 |
| GB | 2360218 | A | 9/2001 |
| GB | 2 507 104 | A | 4/2014 |
| JP | 2003522003 | | 7/2003 |
| JP | 2007509378 | | 4/2007 |
| JP | 2014083446 | A | 5/2014 |
| WO | WO/1995/022365 | A1 | 8/1995 |
| WO | WO 1995/022365 | A1 | 8/1995 |
| WO | WO 1999/030760 | A1 | 6/1999 |
| WO | WO/1999/063901 | A1 | 8/1999 |
| WO | WO 1999/063901 | A1 | 12/1999 |
| WO | WO 1999/064095 | A2 | 12/1999 |
| WO | WO 2000-032088 | A1 | 6/2000 |
| WO | WO 2003/063754 | A1 | 8/2003 |
| WO | WO/2003/063754 | A1 | 8/2003 |
| WO | WO 2007-126851 | A2 | 11/2007 |
| WO | WO 2008/057606 | A2 | 5/2008 |
| WO | WO/2009/003989 | A1 | 1/2009 |
| WO | WO 2009/071517 | A1 | 6/2009 |
| WO | WO 2009-140251 | A2 | 11/2009 |
| WO | WO 2010/075240 | A1 | 7/2010 |
| WO | WO 2012/068214 | A1 | 5/2012 |
| WO | WO 2014-049086 | A1 | 4/2014 |
| WO | WO 2014/060269 | A1 | 4/2014 |
| WO | WO 2014-106096 | A1 | 7/2014 |
| WO | WO 2015/154864 | A2 | 10/2015 |
| WO | WO 2015/154865 | A2 | 10/2015 |
| WO | WO/2016/043601 | A1 | 3/2016 |
| WO | WO/2017/005605 | A1 | 1/2017 |
| WO | WO/2017/051389 | A1 | 3/2017 |
| WO | WO/2017/129521 | A1 | 8/2017 |
| WO | WO/2017/141194 | A1 | 8/2017 |
| WO | WO/2017/176693 | A1 | 10/2017 |
| WO | WO/2017/176704 | A1 | 10/2017 |
| WO | WO/2017/180980 | A1 | 10/2017 |
| WO | WO/2017/189712 | A1 | 11/2017 |
| WO | WO/2018/128976 | A1 | 7/2018 |
| WO | WO/2018/134552 | A1 | 7/2018 |
| WO | WO/2018/134553 | A1 | 7/2018 |
| ZA | 9900888 | A | 8/1999 |

\* cited by examiner

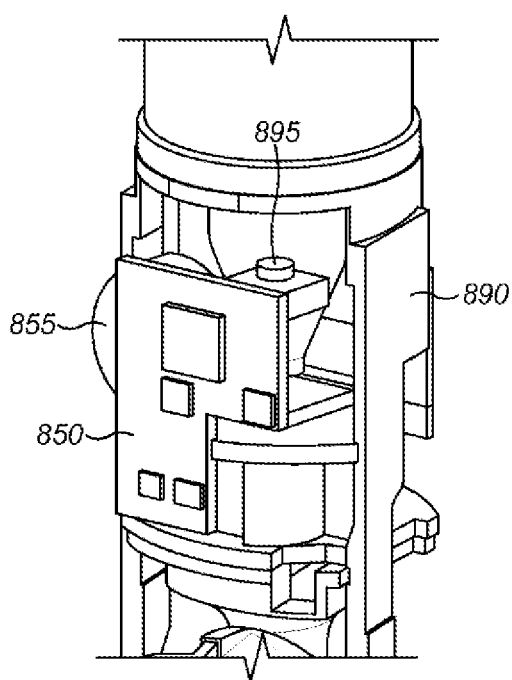
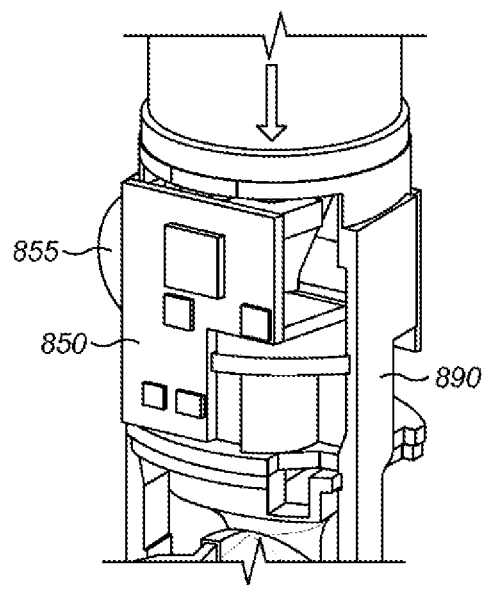
FIG. 8B
FIG. 8C

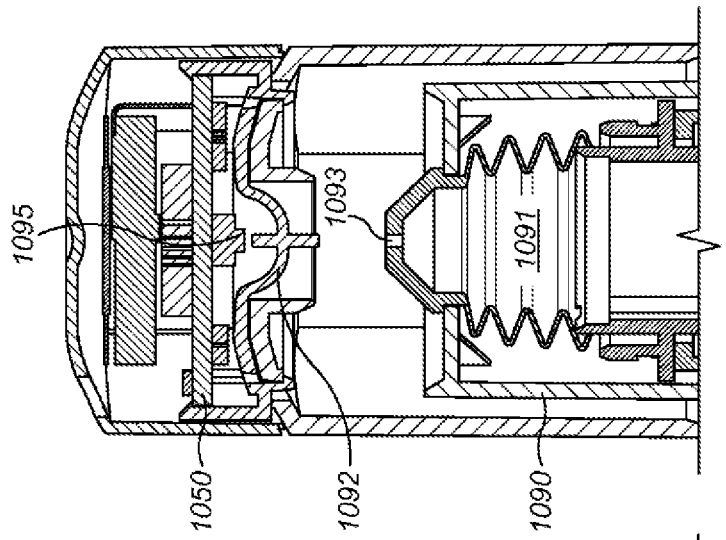
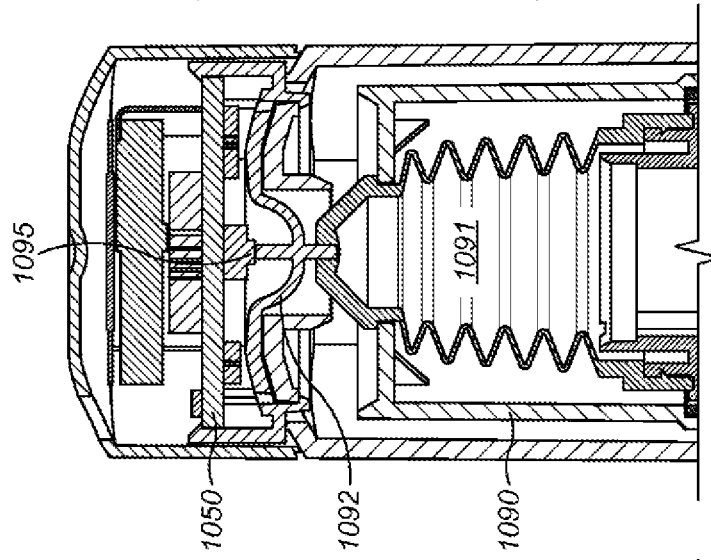
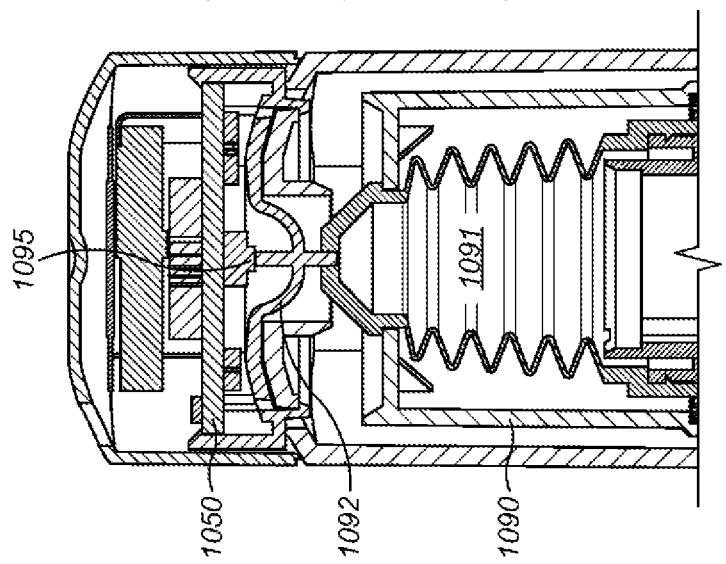

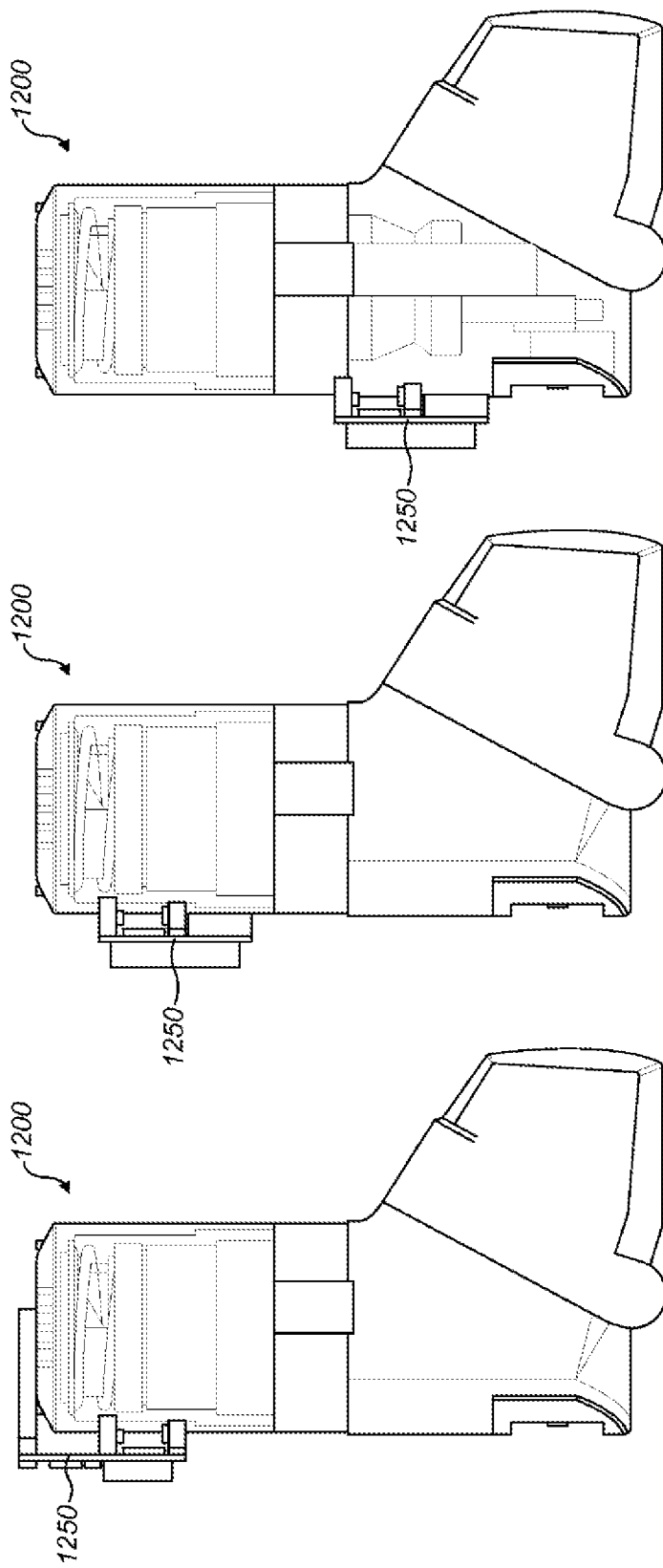

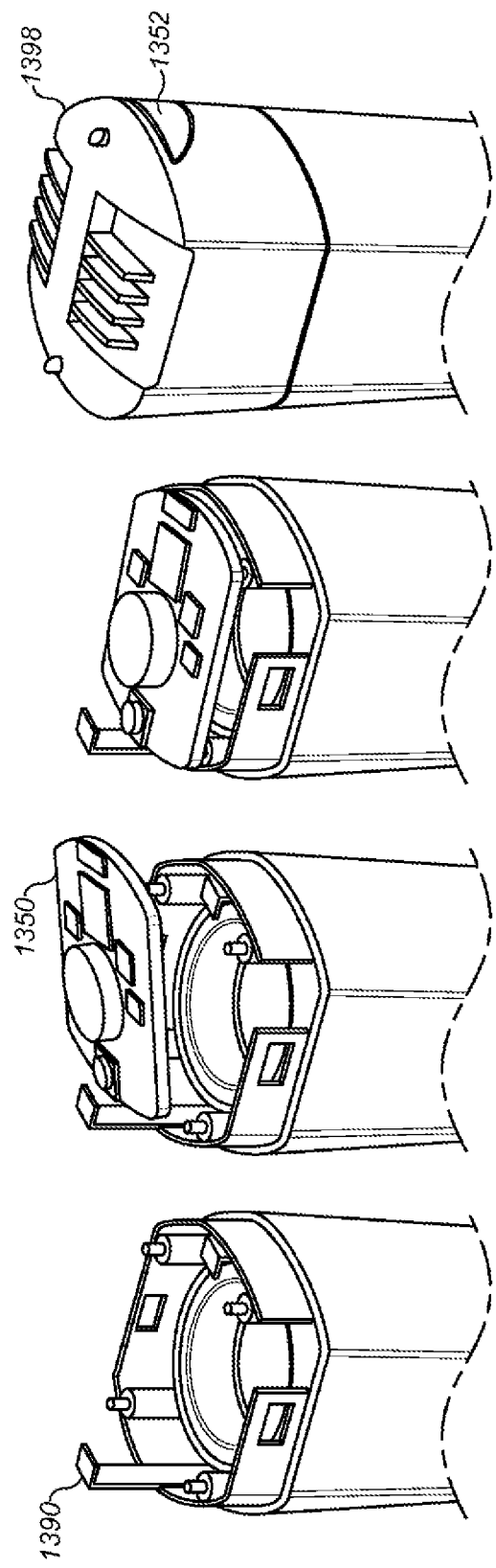

COMPLIANCE MONITORING MODULE FOR A BREATH-ACTUATED INHALER

This application is a continuation of U.S. patent application Ser. No. 15/681,126, filed Aug. 18, 2017, which is a continuation of U.S. patent application Ser. No. 15/155,808, filed May 16, 2016, now issued as U.S. Pat. No. 9,782,551, on Oct. 10, 2017, which is a continuation of U.S. patent application Ser. No. 15/155,400, filed May 16, 2016, now issued as U.S. Pat. No. 9,782,550, on Oct. 10, 2017, which is a continuation of Patent Cooperation Treaty Application No. PCT/US2015/047366, filed Aug. 28, 2015, which claims priority to U.S. application Ser. No. 62/043,120 entitled COMPLIANCE MONITORING MODULE FOR A BREATH-ACTUATED INHALER filed on Aug. 28, 2014, the contents of which are incorporated fully herein by reference.

The present disclosure generally relates to monitoring of patient compliance to medicament administration via an inhaler. More particularly, the disclosure relates to the use of a miniature pressure sensor for compliance monitoring in a breath-actuated inhaler.

Inhalers or puffers are used for delivering medication into the body via the lungs. They can be used, for example, in the treatment of asthma and chronic obstructive pulmonary disease (COPD). Types of inhalers include metered dose inhalers (MDIs), dry powder inhalers (DPIs) and nebulisers.

Modern breath controlled nebulisers generally fall into one of two categories: breath enhanced or breath actuated. Breath enhanced nebulisers use patient airflow to control the flow of drug-containing aerosol to the patient. Since aerosol is generated continuously in these nebulisers, some is wasted to the environment. Breath actuated nebulisers use inhalation and/or exhalation detection to turn the aerosol generator on and off with patient breathing. This improves efficiency compared to breath enhanced nebulisers, since little if any drug is lost to the environment. Detection in breath actuated devices is usually by heat and/or pressure sensors.

A common problem faced in respiratory drug delivery, regardless of the device used, is how to monitor patient adherence and compliance.

Adherence deals with the patient following the prescription label, for example taking the prescribed number of doses per day. If the prescription calls for two doses each day, and the patient is taking two doses a day, they are considered 100% adherent. If the patient is only taking one dose a day, they are only 50% adherent. In the latter case, the patient is not getting the treatment prescribed by their doctor.

Compliance, on the other hand, relates to how the patient uses their drug delivery device. If used in the manner recommended for effective treatment, they are 100% compliant. If not used properly however, they are less than 100% compliant. Use of a breath-actuated inhaler involves inhaling in a particular way; for example the inhalation may need to be long enough and hard enough to entrain a full dose of medicament. For some patients, for example children and the elderly, meeting the requirements for full compliance may be difficult. However, failing to achieve 100% compliance can reduce the effectiveness of the prescribed medicament. When a doctor prescribes a medication, the efficacy of that treatment is totally dependent on the patient using their device properly and the proper number of times each day. If they fail to do so, the patient is likely to experience no improvement in their condition. Absent any means of verifying patient adherence/compliance, yet faced with a patient for whom no improvement can be seen, the doctor may have no choice but to prescribe a stronger dose or even a stronger medication. In some cases, this may put the patient at risk. This could be avoided if the doctor had some way of confirming that the patient was actually getting the medication prescribed.

The approach followed by some pharmaceutical companies has been to add integral dose counters to their drug delivery products. For example, a dose counter may be triggered by the press of an actuation button or the opening of a cap or cover. Some breath-actuated inhalers comprise adherence dose counters triggered by opening of an aerosol valve, indicating that the patient has inhaled hard enough to release a dose of medicament. While this provides patients and caregivers objective evidence that a device has been used, it still fails to provide any kind of compliance information. There is no means of determining whether the user has inhaled the entire dose, or whether they have inhaled only enough to actuate the aerosol valve and then ceased inhalation or reduced the strength of their inhalation below a level at which drug can be entrained into the airflow. As such, there is a need for a product that provides not only adherence information, but compliance information as well.

A spirometer is an apparatus for measuring the volume of air inspired and expired by a patient's lungs. Spirometers measure ventilation, the movement of air into and out of the lungs. From the traces, known as spirograms, output by spirometers, it is possible to identify abnormal (obstructive or restrictive) ventilation patterns. Existing spirometers use a variety of different measurement methods including pressure transducers, ultrasonic and water gauge.

In order to monitor the flows associated with breathing, a pressure sensor is most convenient because pressure information can be used to determine flow, which can then be used to determine volume.

Pressure sensors used for breath detection generally measure the pressure difference across a section of the airway through which a patient breathes. This is commonly done using two connections, by tubing or other suitable conduits, to connect the sensor to the airway. It is also possible to use a single connection to the airway, with the other port open to the atmosphere. A single port gauge type sensor can also be used if the pressure within the airway is measured both before and after flow is applied, the difference in readings representing the desired pressure drops across the air path resistance. However, the uncertainty associated with the first (no flow) reading is generally high.

Regardless of the pressure sensor type used, pressure sensors are generally connected to patient airways using flexible tubing. A disadvantage of such systems is the possibility of sensor damage related to fluid contamination in the form of spilled drug or patient secretions (mucous, sputum, etc.). In order to isolate the pressure sensor from such contaminants, manufacturers often locate the pressure sensor some distance from the measurement site using elastomeric tubing. However, liquids may still condense within the tubing, creating an environment for bacterial growth in areas exposed to the patient but not generally accessible for cleaning.

Another problem with conventional pressure sensors is thermal drift; the phenomenon by which the pressure reading can change over time with changes in local temperature. It is possible to compensate for such drift using additional circuitry, but this adds cost and volume and increases power requirements. Such circuitry can be located within the pressure sensor itself, but considering that the sensor is generally somewhat removed from the gas being measured, the temperature detected may not be representative of that gas. The temperature monitoring circuitry could be located at the patient, but this adds additional components, plus cost and complexity.

Yet another problem with conventional pressure sensors is susceptibility to high radio frequency (RF) exposure. This can be a real issue when operating in close proximity to a radio transmitter, such as a mobile phone. Other potential sources include wireless communications devices, such as Wi-Fi routers and cordless phones, and various other forms of information technology (IT) equipment such as wirelessly networked printers. Another issue with some conventional pressure sensors is hysteresis, the reluctance of a pressure sensing material such as a diaphragm to return to its original form, shape or position after being deformed. This is observed as a difference in output when passing through the same pressure from different directions (either from above or below the target pressure). When dealing with very low pressure changes, such an offset can be large enough to mask the signal being measured.

There are described herein new means of compliance monitoring using pressure sensing that avoids some or all of the problems described above.

According to a first aspect, there is provided a compliance monitoring module for a breath-actuated inhaler comprising: a miniature pressure sensor, a sensor port of said pressure sensor being configured to be pneumatically coupled to a flow channel through which a user can inhale; a processor configured to: receive a signal originating from a dosing mechanism of the inhaler indicating that medication has been released; receive data from a sensing element of the pressure sensor; and based on said signal from said dosing mechanism and said data from said sensing element, make a determination that inhalation of a breath containing medication through said flow channel complies with one or more predetermined requirements for successful dosing; and a transmitter configured to, responsive to said determination, issue a dosing report.

The miniature pressure sensor could be a microelectromechanical system (MEMS) pressure sensor or a nanoelectromechanical system (NEMS) pressure sensor.

Said one or more predetermined requirements for successful dosing could comprise one or more of: flow rate exceeding a predetermined threshold value; inhalation duration exceeding a predetermined threshold value; flow rate exceeding a predetermined threshold value for at least a predetermined threshold duration; total volume inhaled exceeding a predetermined threshold value; and peak inspired flow (PIF) exceeding a predetermined threshold value.

The module could be configured for use with an inhaler comprising means for user-actuated priming of the dosing mechanism, and means for breath-actuated release of medicament.

Said signal originating from the dosing mechanism could be transmitted in response to user-actuated priming of the dosing mechanism.

Said transmitter could be wireless.

The pressure sensor could be a MEMS barometric pressure sensor. The sensor could be a piezo-resistive or capacitive MEMS pressure sensor.

Any two or more of the pressure sensor, processor and transmitter could be comprised in a single integrated circuit or System on Chip (SoC).

The module could further comprise said flow channel, the pressure sensor being located inside the flow channel, the pressure sensor optionally being located in a recess in an internal wall of the flow channel.

The module could further comprise said flow channel, the pressure sensor being located external to the flow channel and said sensor port being pneumatically coupled to the flow channel via an opening in a wall of the flow channel.

The module could further comprise a seal arranged to pneumatically couple the sensor port to said opening, at least a part of said seal optionally being sandwiched between the pressure sensor and the wall, at least a part of said seal optionally extending from an exterior surface of said wall to a surface on which the pressure sensor is mounted so as to encapsulate the pressure sensor in a pneumatic chamber adjacent the wall.

Said wall and said seal could be formed by a two-shot moulding process. The module could further comprise a thermally conductive gasket sandwiched between the pressure sensor and the wall, said thermally conductive gasket optionally acting as the seal.

The module could further comprise an air-permeable, water-impermeable filter separating said sensor port from said flow channel.

The pressure sensor could comprise a metal housing.

The module could be configured to be affixed to the part of a main body of the inhaler that is uppermost in use, following sterilisation of one or more parts of said main body. Said processor could be comprised in the pressure sensor.

The module could further comprise a data buffer configured to store data received from a sensing element of the pressure sensor. Said data buffer could optionally be comprised in the pressure sensor. Said data buffer could be configured to store data corresponding to one inhalation/exhalation waveform. Said data buffer could be a first in, first out (FIFO) data buffer.

The module could further comprise an additional MEMS barometric pressure sensor configured for monitoring environmental barometric activity.

The transmitter could be comprised in a transceiver configured to communicate data from and/or to the pressure sensor. The transmitter could be wireless. Said wireless transmitter could be a Bluetooth™ subsystem, optionally a Bluetooth™ Low Energy (BLE) integrated circuit or System on Chip (SoC).

The pressure sensor and/or the transmitter could be mounted on a printed circuit board (PCB).

The module could further comprise a battery, optionally a coin cell, arranged to power the pressure sensor.

The pressure sensor could have a sensitivity of 20 Pascals or less.

The pressure sensor could comprise a sensing element. The processor could be configured to poll said sensing element at a frequency of greater than or equal to 100 Hz.

The module could further comprise control means for switching on the pressure sensor and/or waking the pressure sensor from a low power state.

Said control means could be activated by motion of a yoke attached to a mouthpiece cover such that opening of said mouthpiece cover causes said yoke to move in such a way as to activate the control means.

Said control means could be a mechanical switch, an optical sensor, an accelerometer or a Hall effect sensor.

The processor could be configured to respond to said control means switching on and/or waking up the pressure sensor by taking a tare reading from said sensing element and calibrating data received from the sensing element subsequently using said tare reading.

The processor could be configured to determine a dynamic zero from a moving average of measurements by the pressure sensor, and dynamically calibrate the pressure sensor according to said dynamic zero.

The processor could be configured to filter out electrical noise inherent to the pressure sensor and/or environmental anomalies in data received from a sensing element of the pressure sensor.

The module could further comprise a temperature sensor, optionally integral with the pressure sensor. The processor, optionally comprised in one of the pressure and temperature sensors, could be configured to apply temperature compensation determined from data received from a sensing element of the temperature sensor to data received from a sensing element of the pressure sensor.

The inhaler could further comprise a mouthpiece, said sensor port being pneumatically coupled to a flow channel in pneumatic communication with said mouthpiece.

According to a second aspect there is provided a breath-actuated inhaler comprising the module of the first aspect.

According to a third aspect there is provided an inhaler accessory comprising the module of the first aspect, configured to be connected to an inhaler such that said sensor port is pneumatically coupled to a flow channel in pneumatic communication with a mouthpiece of said inhaler.

According to a fourth aspect there is provided a method for monitoring patient compliance to medicament administration via a breath-actuated inhaler comprising: receiving a signal originating from a dosing mechanism of the inhaler indicating that medication has been released; a miniature pressure sensor, a sensor port of said sensor being pneumatically coupled to a flow channel through which a user can inhale, sensing a pressure change at said sensor port; receiving data from a sensing element of the sensor; based on said signal from said dosing mechanism and said data from said sensing element, making a determination that inhalation of a breath containing medication through said flow channel complies with one or more predetermined requirements for successful dosing; and responsive to said determination, transmitting a dosing report.

The miniature pressure sensor could be a microelectromechanical system (MEMS) pressure sensor or a nanoelectromechanical system (NEMS) pressure sensor. The MEMS pressure sensor could be a MEMS barometric pressure sensor. The sensor could be a piezo-resistive or capacitive MEMS pressure sensor. Said one or more predetermined requirements for successful dosing could comprise one or more of: flow rate exceeding a predetermined threshold value; inhalation duration exceeding a predetermined threshold value; flow rate exceeding a predetermined threshold value for at least a predetermined threshold duration; total volume inhaled exceeding a predetermined threshold value; and peak inspired flow (PIF) exceeding a predetermined threshold value.

The method could further comprise: monitoring environmental barometric activity using an additional MEMS barometric pressure sensor; and calibrating said sensor having the sensor port pneumatically coupled to said flow channel against said additional sensor. The method could further comprise: switching on the sensor or waking the sensor from a low power state; in response to the sensor switching on or waking up, taking a tare reading from a sensing element of the sensor; and calibrating data received from the sensing element subsequently using said tare reading.

The method could further comprise: determining a dynamic zero from a moving average of measurements by the sensor; and dynamically calibrating the sensor according to said dynamic zero.

The method could further comprise applying temperature compensation to data received from a sensing element of the pressure sensor using data received from a sensing element of a temperature sensor.

The method could further comprise storing data received from a sensing element of the sensor in a data buffer. Said data could correspond to one inhalation/exhalation waveform.

Said transmitting could be wireless. Said wireless transmitting could use a Bluetooth™ protocol, optionally the Bluetooth™ Low Energy (BLE) protocol.

The method could further comprise the processor polling a sensing element of the sensor at a frequency of greater than or equal to 100 Hz.

The method could further comprise filtering out inherent electrical noise and/or environmental anomalies in data received from a sensing element of the sensor.

The method could further comprise determining the volume of air inspired or expired by a user of the inhaler from data sensed by a sensing element of the sensor.

According to a fifth aspect there is provided a computer program product comprising instructions for execution by a computer processor to perform the method of the fourth aspect.

According to a sixth aspect, there is provided a compliance monitoring module substantially as herein described with reference to the accompanying figures.

According to a seventh aspect, there is provided an inhaler substantially as herein described with reference to the accompanying figures. According to an eighth aspect, there is provided an inhaler accessory substantially as herein described with reference to the accompanying figures.

According to a ninth aspect, there is provided a method substantially as herein described with reference to the accompanying figures.

According to a tenth aspect, there is provided a computer program product substantially as herein described with reference to the accompanying figures.

Examples of the present invention will now be described with reference to the accompanying drawings, in which.

Figure 7A:
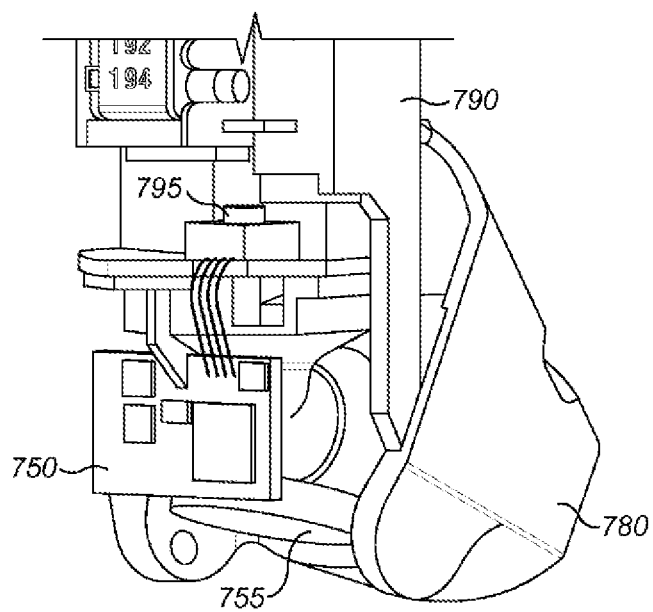
Figure 7B:
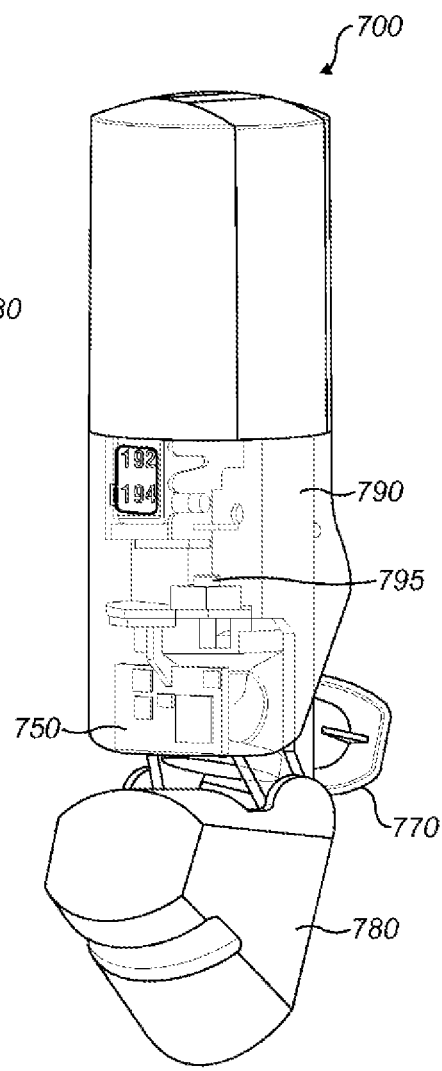
Figure 14:
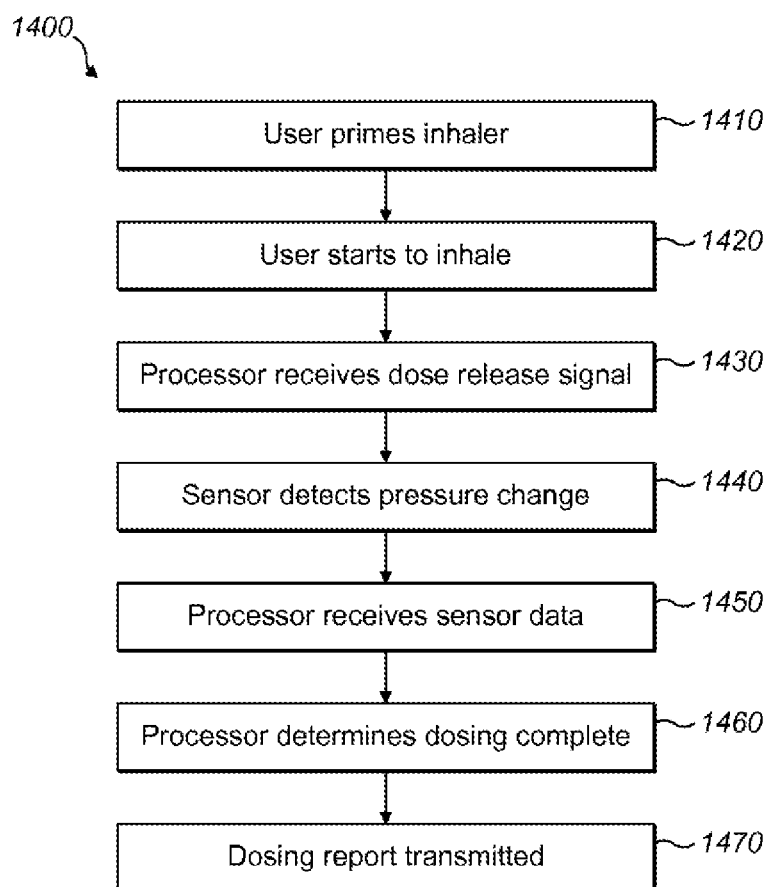
Figure 15:
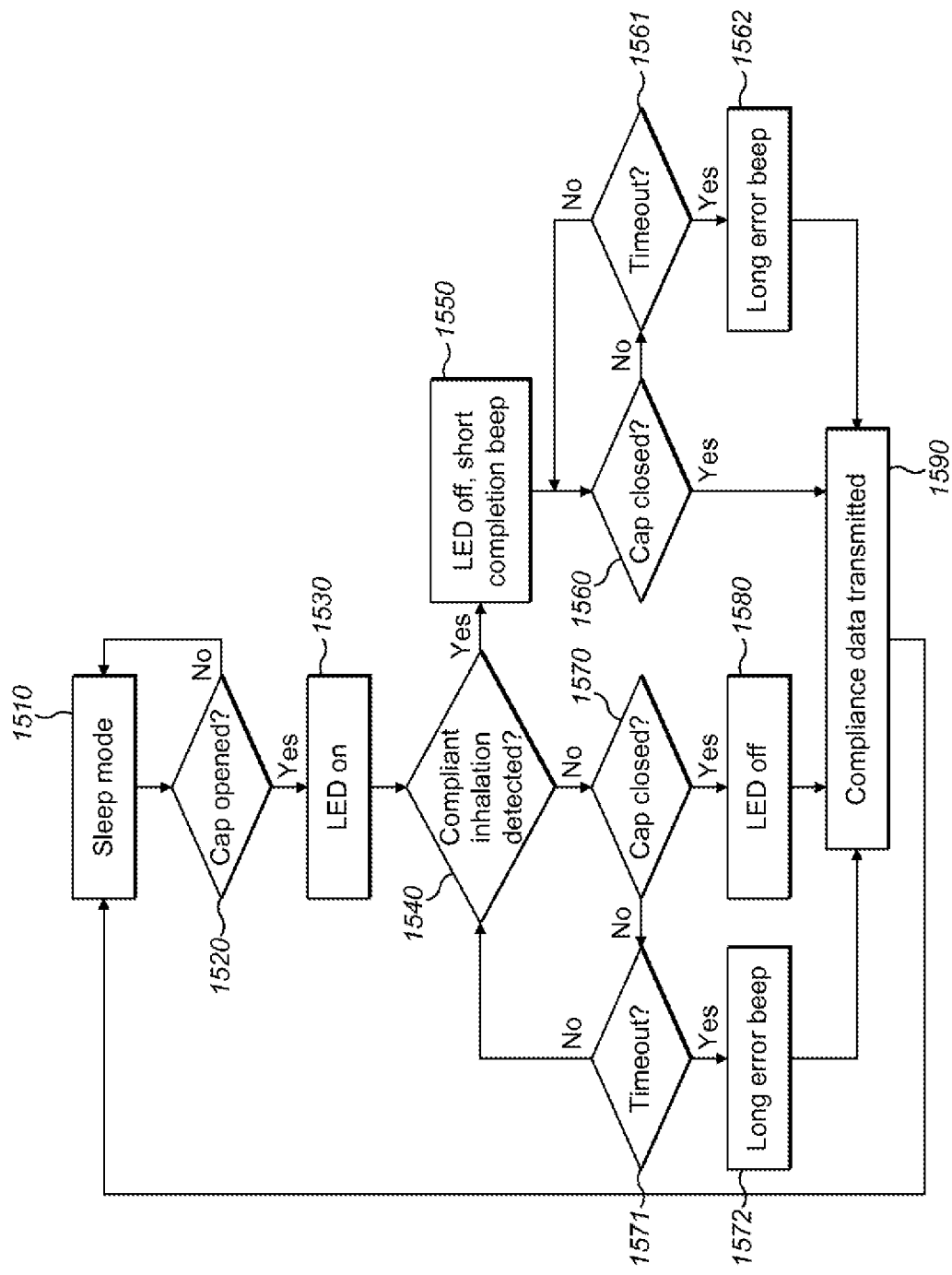

FIGS. 7A, 7B; 8A, 8B, 8C; 9; 10A, 10B, 10C; 11; 12A, 12B, 12C; [to] and 13A, 13B, 13C illustrate example configurations of compliance modules in inhalers;

FIG. 14 is a flowchart illustrating an example compliance monitoring method;

FIG. 15 is a flowchart illustrating example user-device interactions; and

Figure 16A:
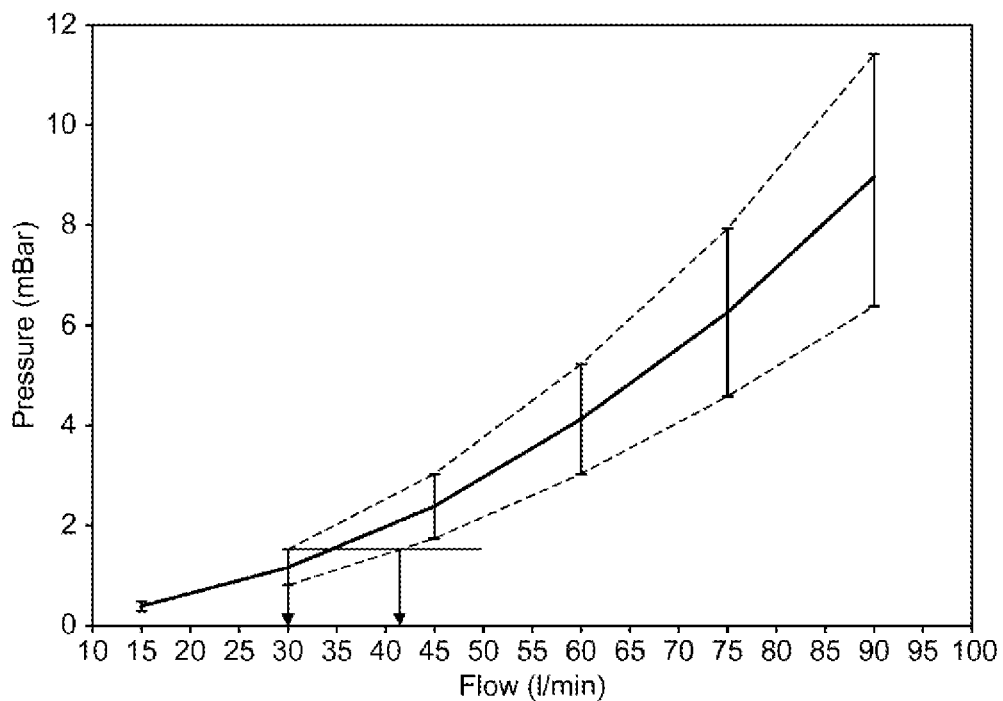
Figure 16B:
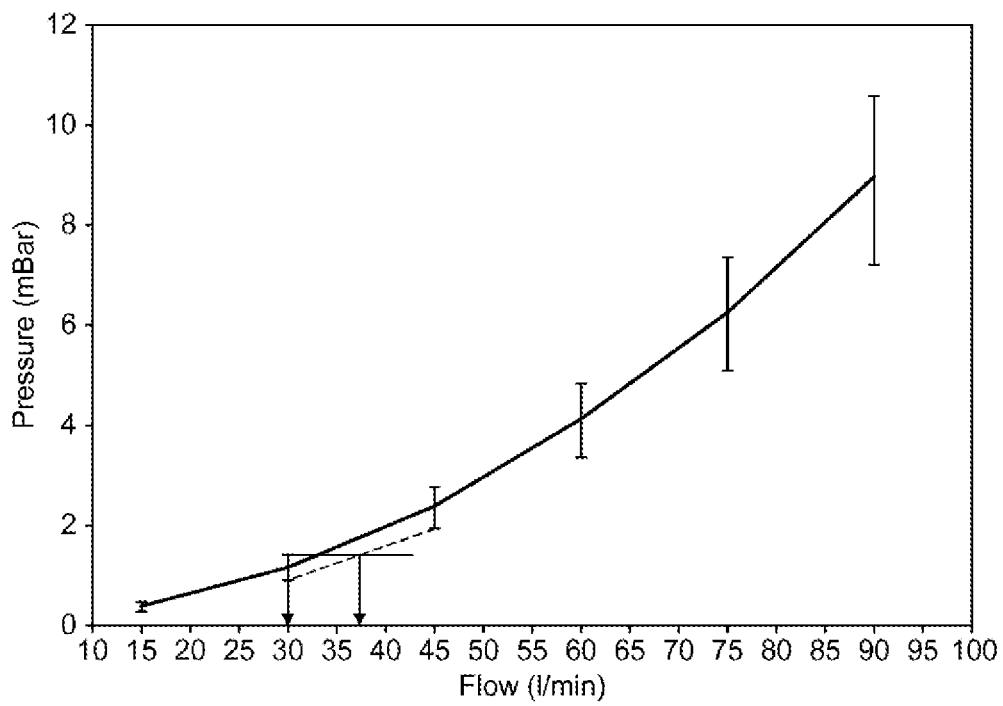

FIGS. 16A and 16B are graphs showing test data.

Elements shown in the Figures are not drawn to scale, but only to illustrate operation. Like elements are indicated by like reference numerals.

In addition to the differential (two port) type pressure sensors and the single port gauge type sensors, with separate measurements made before and after use, discussed above, absolute or barometric pressure sensors are available. Barometric pressure sensors are referenced to vacuum. They are sometimes referred to as altimeters since altitude can be deduced from barometric pressure readings. Sensors of this type have not generally been considered for use in breath detection because of their extremely wide range (20 to 110 kPa) and low resolution. Considering how a typical breath profile may generate pressure changes of the order of only 0.2 kPa, this would require operating the sensor over an extremely narrow portion of its operating range.

However, with miniaturisation, including the introduction of MEMS and NEMS technologies, much improved sensors are now available. A typical MEMS barometric sensor is capable of operation from 20 kPa to 110 kPa and can detect flow rates of less than 30 lpm (litres per minute) when pneumatically coupled to a flow path having a known flow resistance.

Using a barometric sensor enables use of the barometric pressure as a baseline throughout the measurement cycle, thereby addressing the uncertainty of other single port approaches. Q Also, having knowledge of the local barometric pressure can provide some insight into patient lung function. It is suspected that changes in atmospheric pressure, such as those associated with approaching storm fronts, may have an effect on patient breathing, possibly even related to asthma and COPD events.

Barometric pressure sensors are already in stressed condition, having an integral reference port sealed within the device under vacuum. This means that they have low hysteresis in the region of interest.

Due to the extremely small size and mass of their sensing elements, MEMS sensors are capable of reacting to extremely small pressure changes. Some are capable of resolving pressure changes as low as 1 Pa.

MEMS pressure sensors can include all of the requisite analogue circuitry within the sensor package. Temperature compensation and/or digital interfaces can also be integrated with the pressure sensor.

For example, the Freescale MPL3115A2 MEMS barometer/altimeter chip (pressure sensor) is digital, using an PC interface to communicate pressure information to a host micro-computer.

MEMS pressure sensors can be packaged in metal. This provides RF shielding and good thermal conductivity for temperature compensation.

MEMS pressure sensors are also low cost, exhibit low power consumption and are very small. This makes them especially suitable for use in portable and/or disposable devices which may, for example, be powered by batteries such as coin cells.

The small size of MEMS pressure sensors makes it easy to incorporate them into existing designs of inhalers. It may be easier to incorporate them in or close to a mouthpiece to more accurately measure the pressure change caused by a patient's inhalation or exhalation.

A miniature barometric pressure sensor can be connected directly to the patient airway using only a small hole to the air path which does not require tubing of any kind. This minimizes the possibility of moisture condensation and potential bacterial growth associated with elastomeric tubing. An internal seal, for example a gel seal, can be included to protect the sensor element from contamination.

Figure 1:
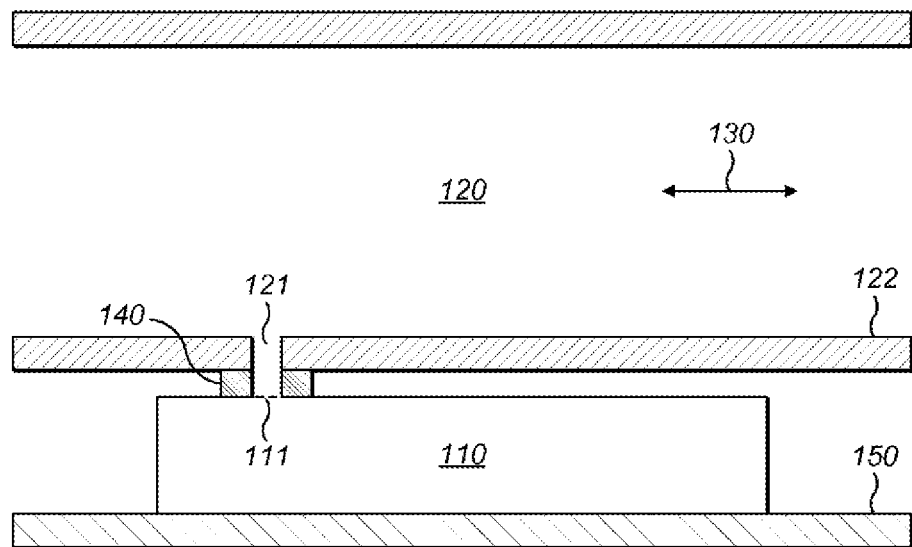
FIGS. 1 to 5 illustrate example arrangements for a miniature pressure sensor for breath detection with respect to a flow channel.

An example of this type of arrangement is shown in FIG. 1. A miniature barometric pressure sensor 110 is placed against the flow channel 120 through which a patient breathes. Airflow is substantially axial as indicated by arrow 130. The sensor port 111 is sealed in line with an opening 121 in flow channel wall 122 by a pneumatic (airtight) seal 140. (Note that, so long as there is a pneumatic connection between the sensor port and the flow channel, the seal need not be completely airtight.) Sensor port 111 optionally comprises a filter, for example an air-permeable, water-impermeable filter. The flow channel and the seal could be formed by a two-shot moulding process. The pressure sensor 110 can be mounted on a printed circuit board (PCB) 150 to provide connection to power sources and other electronics.

Figure 2:
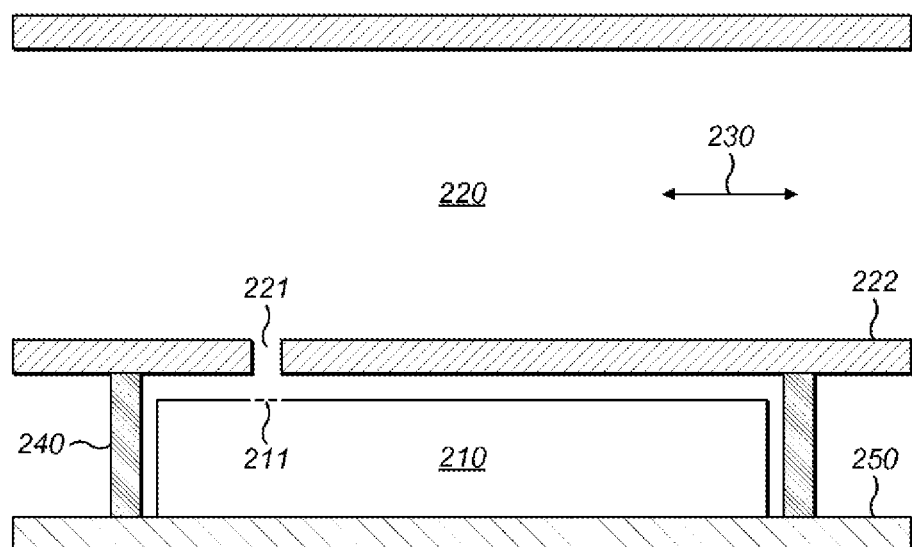

Instead of positioning the seal 140 around the channel between opening 121 and sensor port 111, the entire miniature pressure sensor could be encapsulated within a chamber adjacent to the flow channel as illustrated in FIG. 2. Pneumatic seal 240 is located outside of the sensor footprint and extends all the way from the exterior of flow channel wall 222 to the surface 250 on which the sensor 210 is mounted (for example the component surface of a PCB). FIG. 2 shows a cross-section; pneumatic seal 240 surrounds the perimeter of the sensor 210 whether it is circular, square, rectangular or any other shape. The seal 240, sensor mount 250 and flow channel wall 222 thus form a cavity pneumatically isolated from the external environment except for the flow channel in the location of the opening 221. The pressure at the sensor port 211 is therefore equalized with the pressure in the flow channel at the opening 221.

Since MEMS sensors are available with built-in temperature compensation, there may not be any need for use of external thermal sensors. Compensation can be provided right at the measurement site, increasing the accuracy of the compensation. A MEMS sensor with built-in temperature compensation can also act as a compact breath thermometer, providing further information to the patient and/or their caregiver. If the housing of the sensor is metal, then not only is the sensitive internal circuitry isolated from RF fields, such as those associated with mobile phones or nearby disturbances, but the sensor will also rapidly equilibrate to the local temperature in order to provide optimum temperature compensation.

Figure 3:
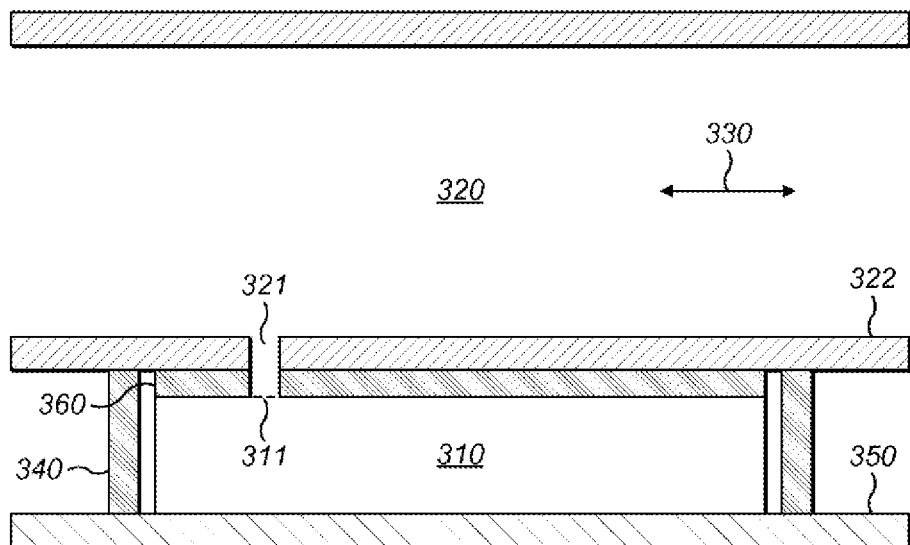

In the embodiments of FIGS. 1 and 2, the miniature sensor is separated from the flow channel wall by an air gap. To improve the ability of the miniature sensor to rapidly detect changes in flow channel temperature, a thermally conductive gasket can be used as shown in FIG. 3. (FIG. 3 is in other respects similar to FIG. 2.)

In the example arrangement of FIG. 3, a thermally conductive gasket 360, such as the silicone types used for transistor heat sinks, is provided between the (optionally metal) housing of the miniature sensor 310 and the flow channel wall 322. The greater the adjacent surface areas covered by the gasket the quicker the temperature equilibration. The gasket 360 could therefore extend over substantially the entire surface of the sensor 310 facing the flow channel wall 322.

Figure 4:
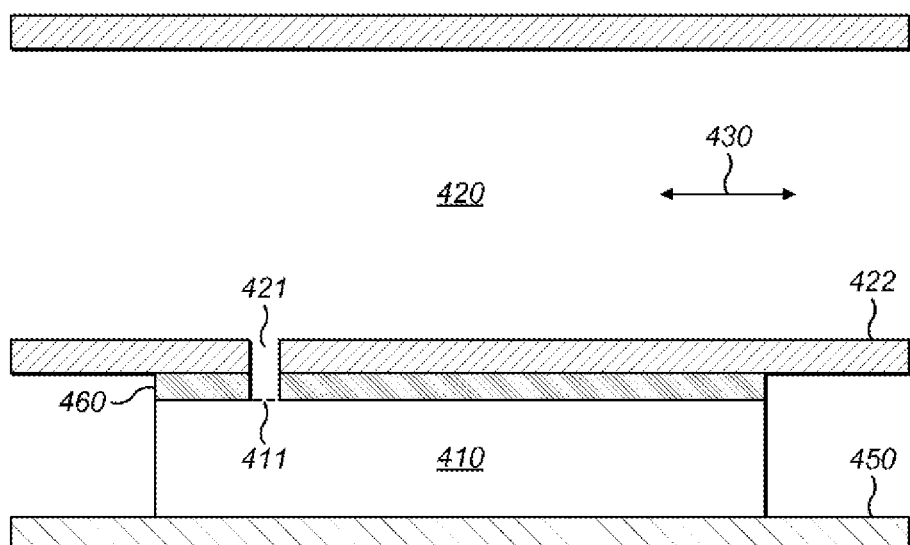

FIG. 4 shows an example arrangement in which a thermally conductive gasket 460 is made of an air-impermeable substance which deforms to the contours of the surfaces of the sensor 410 and flow channel wall 422 it is compressed between. It thus provides a good thermal connection while at the same time acting as a pneumatic seal, eliminating the need for a separate sealing element.

Figure 5:
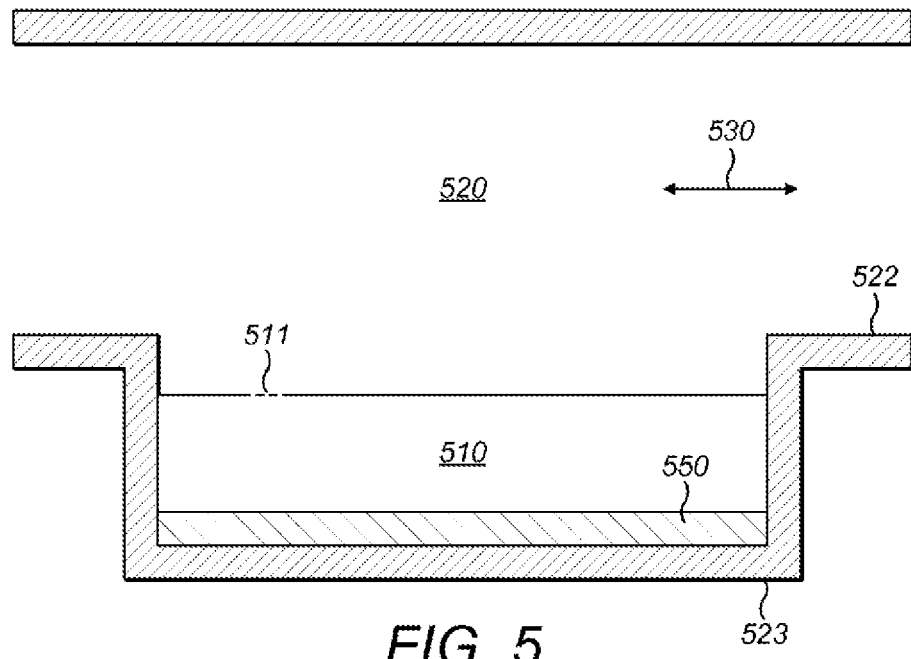

An alternative to positioning the sensor adjacent the flow channel is to place the entire sensor within the low pressure airway of the device to be monitored as illustrated in FIG. 5. For example, the sensor could be placed within the body of a DPI or the 'boot' of a pressurised MDI (pMDI)[ ]. (The term boot refers to the body of the inhaler that generally holds the drug canister.) In this arrangement the sensor is truly measuring the pressure (and optionally, temperature) of the airflow itself, providing improved accuracy. Therefore there is also no need for any sealing element to create a pneumatic conduit between the flow channel 520 and the sensor port 511, or for any thermally conductive gasket to aid in temperature equilibration between them. It is also not necessary to provide the sensor with any access to the external pressure environment for reference purposes because the reference is already built into the sensor itself in the form of a vacuum reference.

In the example of FIG. 5, the miniature barometric pressure sensor 510 is mounted on the interior of flow channel wall 522, optionally via a PCB 550. The flow channel wall 522 may comprise a recessed part 523 in which the sensor 510 is located as shown to reduce disruption to the airflow indicated at 530. For example, the depth of such a recess 523 could be substantially equal to the thickness of the sensor 510 so that the surface of the sensor comprising the sensor port 511 lies flush with the parts of the interior surface of flow channel wall 522 to either side of the sensor 510. Recess 523 could be a volume cut out of the wall 522 or a part of the wall that extends radially outwards relative to the rest as shown.

It should be noted that due to their small size, MEMS pressure sensors can be used to monitor patient flow through, for example, nebulisers, DPIs or pMDIs, thus facilitating low cost compliance monitoring, in addition to/in place of adherence monitoring, which confirms device actuation. Said compliance monitoring could be implemented using an accessory device that couples to the dosing device through a small hole to the airway to be monitored, or in the dosing device itself. The small size, high performance and low cost of MEMS sensors make them ideally suited to such applications where size and weight are major considerations for users who may have to carry their inhaler with them at all times.

Figure 6:
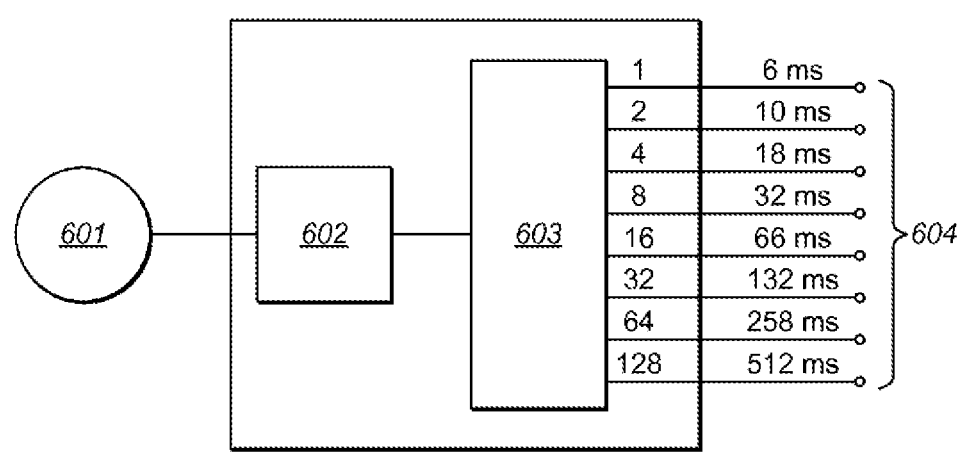
FIG. 6 is a schematic of example sensor electronics.

If output from the miniature pressure sensor is digital, all low level signal processing can be done within the sensor, shielding it from outside interference. This makes it possible to work with signals of the order of tens of Pascals without much difficulty, something that traditional sensors with external circuitry would be challenged to do. FIG. 6 shows schematically some electronic components of an example miniature barometric pressure sensor. Sensor element 601 passes analogue signals to analogue to digital converter (ADC) 602. The digital output signal of ADC 602 is then averaged by a rolling average filter over many cycles to reduce noise. Various averages can be selected under program control in order to balance noise against response time.

As one example, block 603 represents a means of selecting one of eight different oversample (i.e. filter) ratios to output at 604. The fastest response is associated with OSR=1, but this is also the noisiest setting. Conversely, OSR=128 introduces the least noise, but has the slowest response. The optimum setting can be chosen depending on the particular application. With an OSR setting of 16, the output is clean enough and the update time quick enough for most respiratory applications.

It may be desired, for example in order to record patient flow profiles, to create a waveform associated with the real time fluctuations of pressure detected by the sensor. If one were to construct such a waveform from single readings of the sensor each time new data became available, the resulting waveform would exhibit blocky artefacts, rather than a smooth waveform, due to the delays associated with each tap. However, by driving the ADC 602 at a suitable frequency, for example approximately 100 Hz, and reading data at the same rate, the data presented to each tap is further averaged, resulting in a much smoother waveform.

The averaged output can then be passed to a circular first in, first out (FIFO) buffer (not shown) for storage until the data can be processed by a connected processor integrated into the device, or transmitted for offloaded processing. Such a FIFO buffer could, for example, store a number of samples approximately equivalent to, or a little greater than, one typical breath waveform to ensure that an entire inhalation/exhalation profile can be captured. Using a buffer reduces the demand on the serial port of the sensor in cases where the waveform is not required in real time. With the addition of communications it is possible to monitor patient adherence and compliance and communicate such information, for example including patient flow profiles, to a user device such as a smart phone or tablet. From a user device data can optionally be communicated to a caregiver's device, for example a doctor's personal computer (PC). This could be done using a wired connection, for example via a Universal Serial Bus (USB) port. Alternatively, using wireless technology, it is possible to communicate results to the outside world without interrupting the product housing in any significant way. Suitable wireless technologies could include, for example, WiFi technologies such as IEEE 802.11, Medical Body Area Network (MBAN) technologies such as IEEE 802.15, Near Field Communication (NFC) technologies, mobile technologies such as 3G and Bluetooth™ technologies such as Bluetooth™ Low Energy (BLE). A wireless transceiver, for example in the form of a BLE chip, could be connected to the miniature sensor or integrated with it.

Such wireless connectivity could be used, for example, to report device actuation and/or sensed inhalation with date and time stamps in real time. This data could be processed externally and if the result of such processing is that it is determined that a prescription should be refilled, an alert can be sent to the patient and/or caregiver and/or pharmacist. Alerts could be provided via one or more user interfaces of the inhaler (for example an LED and/or a buzzer) or via text message or email. As another example, if no dosing report is received within a predetermined period following a scheduled dosing time, a reminder could be sent to the patient and/or caregiver. Alerts could also be generated for example if use frequency is exceeding a safe threshold. The compliance module could communicate directly or indirectly with one or more of: a user device (such as a mobile phone e.g. a smartphone, a tablet, a laptop or a desktop computer) of a patient, or of a caregiver (such as a doctor, nurse, pharmacist, family member or carer), a server e.g. of a health service provider or inhaler or drug manufacturer or distributor or a cloud storage system. Such communication could be via a network such as the Internet and may involve a dedicated app, for example on the patient's smartphone.

Compliance monitoring means (such as one or more sensors, e.g. a device actuation sensor such as a mechanical switch to detect adherence and compliance reporting means, e.g. a miniature pressure sensor to detect sufficient flow for proper dose delivery) and compliance reporting means (such as a wireless transmitter or wired output port) could be included in a single module. This module could be sold as a separate inhaler accessory/upgrade for attachment to an existing or slightly modified design of inhaler. Alternatively, the compliance monitoring module could be incorporated into the inhaler during manufacture. It is not required for all components of the compliance monitoring module to be comprised in a single physical unit, though this may be the case. In the case of an inhaler accessory version, the module could consist of one or more attachable units. In the case of a module incorporated into an inhaler, the individual components could be located in any suitable locations in or on the inhaler and need not be grouped together or connected any further than required for them to function.

The sensor could, for example, be used in the types of breath actuated dry powder inhalers described in PCT patent application publications numbers WO 01/97889, WO 02/00281, WO 2005/034833 or WO 2011/054527. These inhalers are configured such that inhalation by the user through the mouthpiece results in an airflow through the device entraining dry powder medicament. The inhalation also results in another airflow entering the inhaler from outside. The inhaler comprises a swirl chamber in which the two airflows collide with one another and the chamber walls to break down aggregates of the dry powder medicament for more effective delivery.

These inhalers comprise a dose counting mechanism for determining that a bolus of powder has been metered from a hopper into a dosing chamber following priming by a user. The dose metering system includes a pawl movable along a predetermined path during the metering of a dose of medicament to the mouthpiece by the dose metering system. The dose counter includes a bobbin, a rotatable spool, and a rolled ribbon received on the bobbin, rotatable about an axis of the bobbin. The ribbon has indicia thereon successively extending between a first end of the ribbon secured to the spool and a second end of the ribbon positioned on the bobbin. The dose counter also includes teeth extending radially outwardly from the spool into the predetermined path of the pawl so that the spool is rotated by the pawl and the ribbon advances onto the spool during the metering of a dose to the mouthpiece.

However, these inhalers do not comprise any means of determining whether the dose has been successfully administered. The addition of a miniature barometric pressure sensor anywhere in the airflow path through the inhaler or anywhere in fluid communication with the airflow path could enable compliance monitoring since such a miniature sensor could collect sufficient data to indicate whether or not the patient inhaled in an appropriate manner (e.g. hard enough and for long enough) to receive a full dose of medicament.

This information, combined with a signal originating from the dose metering system indicating that a bolus of medicament was made available to the flow channel through which the patient inhales prior to the inhalation, is sufficient to confirm that a dose has been successfully administered.

A signal could be obtained from the dose metering system in any convenient manner. For example, an electronic switch could be arranged such that it is actuated by motion of the pawl or rotation of the spool. This switch could be connected to an input of the processor such that the processor receives an electronic pulse when a dose is metered. FIGS. 7A, 7B; 8A, 8B, 8C; [to] and 9 illustrate further details of how a compliance module could be integrated into such an inhaler.

FIGS. 7A, 7B illustrate[s an] examples in which a PCB 750 carrying a MEMS pressure sensor and optionally a processor and transmitter is incorporated into an inhaler 700 body close to a mouthpiece 770. In FIG. 7A mouthpiece 770 is hidden by a cover 780. In FIG. 7B the cover 780 is pulled down to expose mouthpiece 770. Cover 780 is connected to a yoke 790 such that when cover 780 is swung down to expose mouthpiece 770, yoke 790 is pulled down to close a tactile switch 795. When switch 795 is closed, an electrical connection is formed between PCB 750 and a battery 755, such as a coin cell, so that the PCB 750 is only powered when the mouthpiece cover 780 is open. This helps to conserve battery power for when it is needed. Alternatively, the PCB 750 could always be connected to the battery 755, but closing of switch 795 (or activation of some other switching means, e.g. an optical sensor, an accelerometer or a Hall effect sensor) could wake PCB 750 from a power-conserving sleep mode.

Figure 8A:
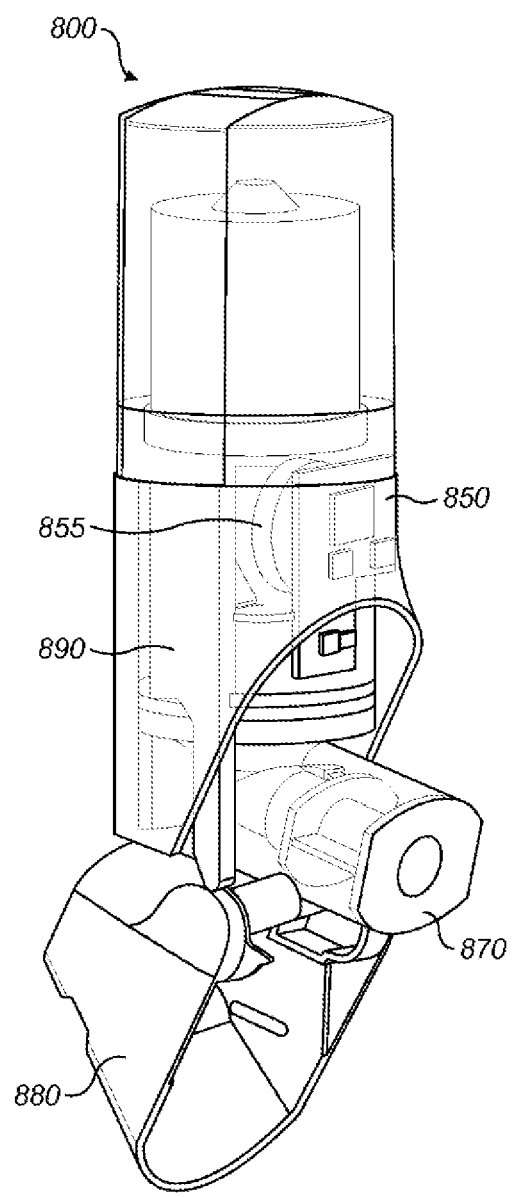

An alternative arrangement is shown in FIG. 8A. Similarly to the example shown in FIG. 7B, a mouthpiece 870 is exposed by swinging down a cover 880 which results in the pulling down of a yoke 890. In this example however, the PCB 850 (again carrying a MEMS pressure sensor and optionally a processor and transmitter) is incorporated into a median portion of the inhaler 800 body. The yoke 890 is formed in an "n" shape to the left and right and above the PCB when the inhaler 800 is oriented for use (with the mouthpiece horizontal at the downward end). FIG. 8B shows an enlarged view of the PCB and yoke when the cover is closed. FIG. 8C shows a similar view when the cover is opened. In FIG. 8C, the horizontal part of the yoke 890 is pulled down to close a tactile switch 895. Similarly to the example of FIG. 7B, when switch 895 is closed, an electrical connection is formed between PCB 850 and a battery 855, such as a coin cell, so that the PCB 850 is only powered when the mouthpiece cover 880 is open. Alternatively, the PCB 850 could always be connected to the battery 855, but closing of switch 895 (or activation of some other switching means, e.g. an optical sensor, an accelerometer or a Hall effect sensor) could wake PCB 850 from a power-conserving sleep mode.

Figure 9:
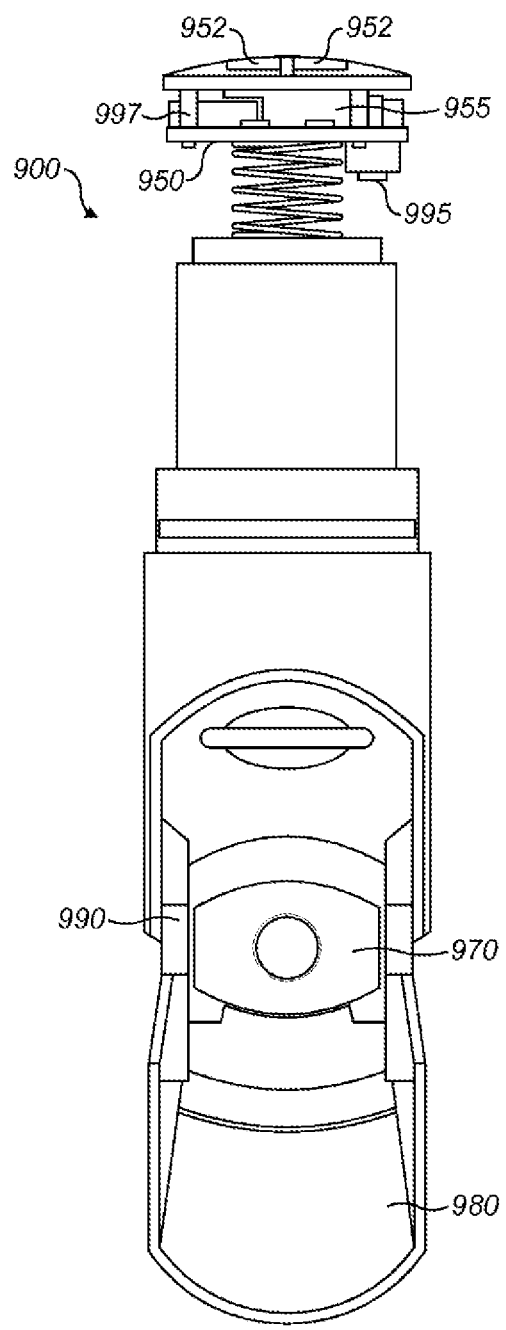

A further alternative arrangement is shown in partially exploded form in FIG. 9. Similarly to the examples shown in FIGS. 7B and 8A, a mouthpiece 970 is exposed by swinging down a cover 980 which results in the pulling down of a yoke 990. In this example however, the PCB 950 (again carrying a MEMS pressure sensor and optionally a processor and transmitter) is incorporated into the top of the inhaler 900 body. A collar 997 around the PCB 950 is clipped onto the top of the yoke (not shown) towards the end of manufacture of the inhaler 900. This can be done following sterilisation of parts of the inhaler body. This is advantageous since the sterilisation process could damage the sensitive electronics on the PCB 950. In this example the yoke 990 is configured to rise when the mouthpiece cover 980 is opened. This pushes the horizontal top part of the yoke 990 (which is similar to that shown in FIG. 8B) up to close tactile switch 995. Similarly to the examples of FIGS. 7A, 7B, and 8C, when switch 995 is closed, an electrical connection is formed between PCB 950 and a battery 955, such as a coin cell, so that the PCB 950 is only powered when the mouthpiece cover 980 is open. Alternatively, the PCB 950 could always be connected to the battery 955, but closing of switch 995 (or activation of some other switching means, e.g. an optical sensor, an accelerometer or a Hall effect sensor) could wake PCB 950 from a power-conserving sleep mode.

Indicator light emitting diodes (LEDs) visible through (optionally coloured) windows or light pipes 952 shown on the exterior of the inhaler 900, preferably in a position visible to a user during dosing, are also powered by battery 955 and can be controlled by a processor on the PCB. LEDs 952 can be used to provide information to a user and/or caregiver by indicating, for example with different colour and flash combinations, that e.g. the mouthpiece cover is open (and therefore the inhaler is primed for dosing) and/or it is time to refill a prescription and/or that (according to processing of the pressure sensor readings) dosing is complete/has not been fully completed.

Another alternative arrangement is shown in FIGS. 10A, 10B, 10C. In this case yoke 1090, linked to a hinged mouthpiece cap (not shown) carries bellows 1091, made of a partially compliant material.

FIG. 10A shows the bellows position when the cap is closed. A foot of a spring arm 1092 is received in a recess 1093 in the upper wall of the bellows. The bottom of the recess 1093 therefore pushes on the lower surface of the foot such the spring arm is biased upwards. This causes a head of the spring arm 1092 to close a switch 1095 which keeps PCB 1050 in sleep mode.

FIG. 10A shows the arrangement as opening of the cap is begun, when yoke 1090 and therefore bellows 1091 move slightly upwards. Spring arm 1092 remains contacting the switch 1095 and the compliance of the bellows material relieves any additional strain which would otherwise be put on the switch since the bottom of recess 1093 bends to take the strain.

FIG. 10C shows the arrangement when the cap is fully open. The yoke 1090 and bellows 1091 have moved down clear of the spring arm 1092, which relaxes down away from switch 1095. Switch 1095 is therefore opened, waking the PCB 1050.

Optionally, a grub screw may be included to fine tune the contact between the switch and spring arm.

As another example, the sensor could be used in the types of breath actuated pressurised aerosol inhalers described in PCT patent application publication numbers WO 01/93933 or WO 92/09323. These inhalers comprise a means for releasing a measured dose of medicament, the releasing means comprising a means for priming the device by applying a preload capable of actuating delivery means, a means for applying a resisting pneumatic force capable of preventing actuation of the delivery means and a release device capable of freeing the resisting pneumatic force to allow the preload to actuate the delivery means and dispense the medicament. The pneumatic resisting force can be established by mechanisms comprising, for example, a diaphragm, a piston cylinder, a bellows or a spring. Inhalation through a valve or past a vane mechanism allows the preload to actuate an aerosol valve to release medicament. While adherence could be monitored for such inhalers by determining when the device is primed and/or when the aerosol valve opens, they do not comprise any means of determining whether the user has inhaled the entire dose. Again, the introduction of a MEMS barometric pressure sensor anywhere in the airflow path through the inhaler or anywhere in fluid communication with the airflow path, in combination with means for determining when the device has been primed and/or when the aerosol valve opens, could enable compliance monitoring.

Priming the device could result in both a preload being applied to the delivery means and a load being applied to an electronic switch. This switch could be connected to an input of the processor such that the processor receives an electronic pulse when the device is primed. Alternatively or additionally, an electronic switch could be arranged to be actuated by motion of the aerosol valve or of the valve or vane mechanism preceding the aerosol valve. This switch could be connected to an input of the processor such that the processor receives an electronic pulse when aerosol is released to the flow channel through which the patient inhales. The switch could be, for example, mechanical, optical, proximity-based or an accelerometer.

Figure 11:
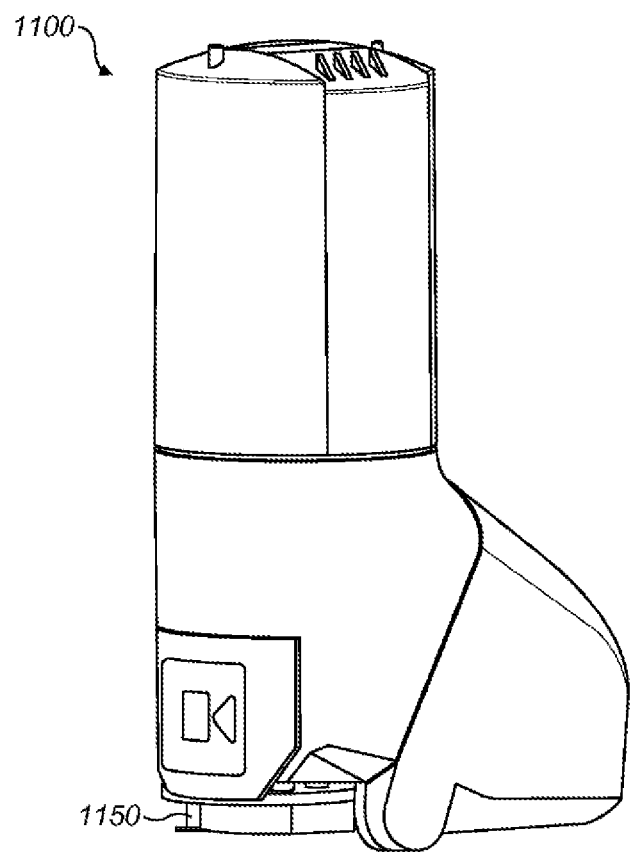

FIGS. 11; 12A, 12B, 12C; Roland 13 illustrate how a compliance module could be integrated into such an inhaler.

FIG. 11 shows a compliance module 1150 located at the base of an inhaler 1100. FIGS. 12A, 12B and 12C show a compliance module 1250 located at the top, median portion and bottom respectively of the back of an inhaler 1200.

The compliance modules of FIGS. 11 and 12A, 12B, and 12C could be added during manufacture of the inhalers, or could be optional accessories which can be clipped onto the inhalers later. That is, the module could be connected (optionally reversibly) to the inhaler via fastening means and be in fluid communication with the inhaler interior and hence the airflow path via one or more apertures in the inhaler body.

Figure 13A:
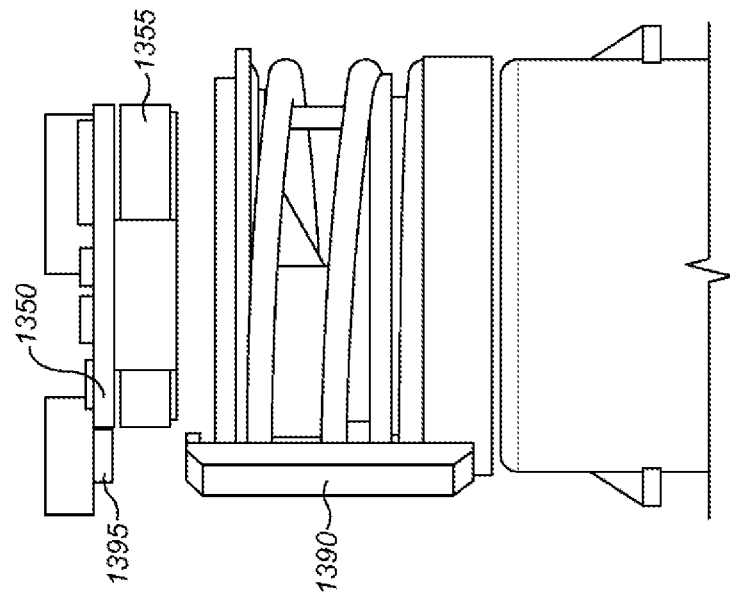
Figure 13B:
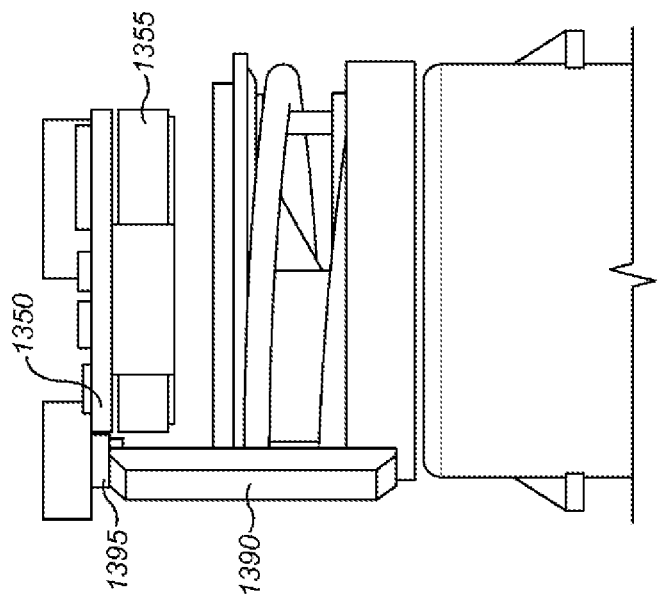

FIGS. 13A, 13B, and 13C illustrate[s] how a compliance module 1350 could be incorporated into the top of an inhaler. FIG. 13A shows the default position of a retainer ring 1390, pushing up onto a tactile switch 1395 to open it. With the switch 1395 open, there is no electrical connection between the compliance module 1350 and a battery 1355 such as a coin cell. FIG. 13B shows the position of retainer ring 1390 when the inhaler is primed for use, lowered with respect to the switch 1395 to close it so that compliance module 1350 is powered. FIG. 13C illustrates the final stages of manufacture of the inhaler shown in FIGS. 13A and B. The compliance module 1350 is lowered onto the inhaler body then a cap 1398 is clipped in place. As with the example of FIG. 9, LED indicators 1352 can be provided.

It should be noted that because MEMS barometric pressure sensors respond to environmental barometric pressure, which can change over time, attention should be paid to the initial reading that any subsequent sensor output signal analysis is based upon. An automatic zero reading (i.e. tare) could be performed immediately prior to monitoring any inhalation signal. While it is possible for this value to change over time in response to changes in local environmental barometric pressure, it would not be expected to cause any issues if a treatment is completed within a few minutes. Alternatively, a second barometer chip could be used to keep track of barometric activity, allowing the primary chip to be used exclusively for breath detection.

The point at which dosing is complete (i.e. where lung volume peaks) could correspond to the point at which flow reverses direction. Thus, the processor can make a determination that dosing is complete when the data from the pressure sensor indicates that flow direction has reversed.

Not all processing needs to be done by the module. Any or all processing could be offloaded to an external data processing device. A wireless scheme (for example comprising a BLE module) could be used to transmit patient flow profiles to an app which could then calculate specific breathing parameters. The inhaler could thereby offload the processing required for such a task to, for example, a smart phone processor. This would facilitate the smallest form factors possible for the inhalers. A further advantage of this approach is that software running on a smart phone can be changed more readily than software running on an inhaler.

FIG. 14 is a flowchart illustrating an example compliance monitoring method. At step 1410 a user primes their inhaler for use, for example by pressing a button or opening a mouthpiece cover. At 1420 the user starts to inhale through a mouthpiece of the inhaler. At 1430 the processor of the compliance module receives a dose release signal. This signal may have been transmitted by the dosing mechanism either in response to priming of the inhaler at 1410 or in response to a pressure sensor or other mechanism sensing that inhalation has begun. For example, inhalation may cause opening of a valve which results in both release of medicament into the flow channel through which the user is inhaling and actuation of an electrical switch to trigger a dose release signal. At 1440 the MEMS pressure sensor detects a pressure change in the flow channel. At 1450 the processor receives data from the sensor. At 1460 the processor determines from the sensor data that one or more predetermined requirements for successful dosing have been met. For example, the sensor data could indicate that flow rate in the flow channel in the inhalation direction exceeded a predetermined threshold value for at least a predetermined threshold duration. Alternatively, the sensor data could be processed such that flow rate is integrated over the time period that the sensor detected inhalation to determine total inhaled volume, and this volume could be compared to a predetermined minimum volume for successful dosing. At 1470 a dosing report is transmitted in response to the processor's determination, for example by a wireless transmitter or via a wired output.

FIG. 15 is flow chart illustrating example control logic for indicating breath actuated inhaler compliance data to both a user and an external entity. The example inhaler is equipped with an indicator LED, a buzzer and a wireless transmitter. It also has a cap linked to a dosing mechanism such that opening the cap primes the inhaler by making a bolus of medicament available to a flow channel through which the user can then inhale. To make the next dose available, the cap must be closed and then opened again. A MEMS pressure sensor is arranged to sense inhalation through the flow channel and a further sensor (e.g. a switch) is arranged to detect opening and closing of the cap.

At 1510 the inhaler is in sleep mode. Opening of the cap at 1520 wakes the inhaler and switches on an LED at 1530. If compliant inhalation (i.e. inhalation meeting whatever criteria are required to confirm dosing is complete) is detected at 1540, at 1550 the LED is switched off and the buzzer issues a brief confirmation beep. If the cap is then closed at 1560, at 1590 compliance data indicating that a dose has been successfully taken and the device shut down correctly is transmitted, e.g. to a device of the user or a caregiver. The inhaler then returns to sleep mode.

If at 1560 the cap is not closed, the device enters a timeout loop at 1561. If timeout occurs, at 1562 a long error beep is issued. Compliance data indicating that a dose has been taken but the device has been left open, and therefore is not ready for subsequent dosing, is then transmitted at 1590 before the inhaler re-enters sleep mode. If the device is a rescue inhaler, for example to be used during an asthma attack, this type of compliance data could indicate that the medication has been successfully taken but has not enabled the user to recover. An automated system could therefore be in place to call paramedics to the user's location (which could for example be known thanks to a GPS tracker in the inhaler or a user device such as a smartphone or tablet in communication with the inhaler).

If compliant inhalation is not detected at 1540, at 1570 it is determined whether the cap has been closed. If not, a timeout loop is entered at 1571 which cycles through 1540, 1570, 1571. If timeout occurs at 1571, at 1572 a long error beep is issued by the buzzer. Compliance data is then transmitted at 1590, indicating that a dose has been loaded but not successfully taken. The inhaler then returns to sleep mode. Again, if the inhaler is a rescue inhaler, transmission of this kind of compliance data could trigger calling of paramedics.

If the cap is closed at 1570, then at 1580 the LED is switched off and at 1590 compliance data is transmitted indicating that a dose has been loaded in error. The inhaler then re-enters sleep mode.

The inhaler may further be capable of determining when inhalation is attempted again following a compliant inhalation without a new dose first being loaded (i.e. without the cap being closed and opened). This could trigger an error beep.

FIGS. 16A and 16B show the mean pressures measured using a miniature relative pressure sensor affixed to the upper part of the casing of 10 different inhalers versus a series of air flow rates applied through the device. Repeat measurements were included for start, middle and end of life of each inhaler (in terms of progress through the number of "shots" before the doses run out). In FIG. 16A, error bars are shown for a +/−3 sigma variation. In FIG. 16B, error bars are shown for a +/−2 sigma variation, capturing a band that 95% of inhalers would fall into. We can thus get an idea of flow uncertainty for pressure measurements by such a sensor used in an inhaler.

For typical inhalation flow rates (30-60l/min), the uncertainty can be calculated from FIG. 16A as ~16 l/min. (The uncertainty in flow rate for each measurement can be estimated as the flow axis differential between the top of the error bar for the measurement and the point at which a line joining the bottoms of the error bars for that measurement and the next reaches the measured pressure. So, for the 30 l/min measurement, the differential is ~41 l/min minus 30 l/min=11 l/min. For 45 l/min the differential is 15 l/min and for 60l/min it is 22 l/min.) The equivalent value taken from FIG. 16B is ~10 l/min. Sufficient precision can thus be obtained to provide useful compliance data.

The above description relates to exemplary uses of the invention, but it will be appreciated that other implementations and variations are possible.

In addition, the skilled person can modify or alter the particular geometry and arrangement of the particular features of the apparatus. Other variations and modifications will also be apparent to the skilled person. Such variations and modifications can involve equivalent and other features which are already known and which can be used instead of, or in addition to, features described herein. Features that are described in the context of separate embodiments can be provided in combination in a single embodiment. Conversely, features which are described in the context of a single embodiment can also be provided separately or in any suitable sub-combination.

What is claimed is:

1. An inhaler for delivering a dose of medicament to treat a respiratory condition, the inhaler comprising:
    a mouthpiece comprising a flow channel through which the dose of medicament can be delivered to a user;
    a barometric pressure sensor pneumatically coupled to the flow channel, wherein the barometric pressure sensor is configured to measure a barometric pressure change within the inhaler resulting from an inhalation or an exhalation into the mouthpiece;
    a processor electrically coupled to the barometric pressure sensor, wherein the processor is configured to determine a value indicative of the inhalation or the exhalation into the mouthpiece based on the pressure change;
    a first housing that includes a reservoir comprising the medicament; and
    a second housing mechanically coupled to the first housing, wherein the second housing includes the barometric pressure sensor and the processor.

2. The inhaler of claim 1, wherein the barometric pressure sensor is further configured to measure a first barometric pressure prior to the inhalation or the exhalation into the mouthpiece and a second barometric pressure during the inhalation or the exhalation into the mouthpiece.

3. The inhaler of claim 1, wherein the first housing is a boot shaped inhaler housing comprising the mouthpiece, and the second housing is disposed at a distal end of the first housing, the distal end being opposite to the mouthpiece.

4. The inhaler of claim 1, further comprising an indicator, wherein the processor is configured to change a status of the indicator based on the pressure change or the value indicative of the inhalation or the exhalation.

5. The inhaler of claim 1, further comprising the medicament, wherein the medicament comprises one or more of salbutamol sulfate, fluticasone propionate, salmeterol, or beclomethasone.

6. The inhaler of claim 1, wherein the inhaler further comprises a wireless transmitter;
   wherein the processor is further configured to calculate a patient flow profile based on the pressure change to create a waveform associated with fluctuations of pressure detected by the barometric pressure sensor; and
   wherein the wireless transmitter is configured to transmit the patient flow profile to a user device comprising a smartphone, a tablet, a laptop, or a desktop computer.

7. The inhaler of claim 1, further comprising a mouthpiece cover, wherein the dose of medicament is made available to the flow channel based on movement of the mouthpiece cover.

8. A method of operating an inhaler having a mouthpiece and a flow channel for delivering a dose of medicament to a user, the method comprising:
   priming the inhaler for use to make the dose of medicament available to the flow channel;
   measuring a barometric pressure change outside of the flow channel resulting from an exhalation into the mouthpiece; and
   determining a value indicative of the exhalation into the mouthpiece based on the pressure change.

9. The method of claim 8, further comprising measuring a first barometric pressure prior to the exhalation into the mouthpiece and a second barometric pressure during the exhalation into the mouthpiece.

10. The method of claim 8, further comprising changing a status of an indicator disposed on the inhaler based on the pressure change or the value indicative of the exhalation.

11. The method of claim 8, further comprising actuating a switch disposed on the inhaler based on movement of a mouthpiece cover and changing a status of the indicator based on actuation of the switch, wherein changing the status of the indicator comprises changing a color or illumination of a light.

12. The method of claim 8, further comprising transmitting the pressure change or the value indicative of the exhalation to a user device comprising a smartphone, a tablet, a laptop, or a desktop computer.

13. The method of claim 8, wherein the medicament comprises one or more of salbutamol sulfate, fluticasone propionate, salmeterol, or beclomethasone.

14. A medicament delivery system comprising:
   an inhaler for delivering a dose of medicament to treat a respiratory condition,
   wherein the inhaler comprises:
      a mouthpiece;
      a flow channel through which the dose of medicament can be delivered to a user when the user inhales through the mouthpiece;
      a barometric pressure sensor pneumatically coupled to the flow channel, wherein the barometric pressure sensor is configured to measure a barometric pressure change outside of the flow channel resulting from an inhalation or an exhalation into the mouthpiece;
      a processor electrically coupled to the barometric pressure sensor, wherein the processor is configured to determine a value indicative of the inhalation or the exhalation into the mouthpiece based on the pressure change; and
      a wireless transmitter configured to transmit the value indicative of the inhalation or the exhalation;
   a smartphone application residing on a smartphone configured for wireless communication with the inhaler, wherein the smartphone application is further configured to receive the value indicative of the inhalation or the exhalation from the inhaler.

15. The medicament delivery system of claim 14, wherein the inhaler further comprises a mouthpiece cover;
   wherein the processor is configured to generate a time stamp when the mouthpiece cover is moved to expose the mouthpiece;
   wherein the wireless transmitter is configured to transmit the time stamp; and
   wherein the smartphone application is further configured to receive the time stamp.

16. The medicament delivery system of claim 14, wherein the inhaler comprises medicament, and wherein the medicament comprises one or more of salbutamol sulfate, fluticasone propionate, salmeterol, or beclomethasone.

17. The medicament delivery system of claim 14, wherein the inhaler further comprises a mouthpiece cover, and
   wherein the inhaler is configured to make the dose of medicament available to the flow channel based on movement of the mouthpiece cover.

18. The medicament delivery system of claim 14, wherein the inhaler further comprises a mouthpiece cover; and
   wherein the pressure sensor is configured to change from a first state to a second state associated when the mouthpiece cover is moved to expose the mouthpiece, wherein the first state is an off state or a sleep state, and the second state is an on state.

19. The medicament delivery system of claim 14, wherein the inhaler further comprises:
   a first housing that includes a reservoir comprising the medicament; and
   a second housing mechanically coupled to the first housing, wherein the second housing includes the barometric pressure sensor and the processor.

20. The medicament delivery system of claim 14, wherein the processor is further configured to record a patient flow profile based on the pressure change, wherein the wireless transmitter is configure to transmit the patient flow profile, and wherein the smartphone application is configured to receive the patient flow profile.

* * * * *